US006949664B2

(12) United States Patent
Petasis

(10) Patent No.: US 6,949,664 B2
(45) Date of Patent: Sep. 27, 2005

(54) TRIHYDROXY POLYUNSATURATED EICOSANOIDS

(75) Inventor: Nicos A. Petasis, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 75 days.

(21) Appl. No.: 10/405,924

(22) Filed: Apr. 1, 2003

(65) Prior Publication Data

US 2003/0236423 A1 Dec. 25, 2003

Related U.S. Application Data

(60) Provisional application No. 60/369,543, filed on Apr. 1, 2002.

(51) Int. Cl.$^7$ ............................................. C07C 57/00
(52) U.S. Cl. ..................................... 554/224; 514/549
(58) Field of Search .......................... 554/224; 514/549

(56) References Cited

U.S. PATENT DOCUMENTS

| 4,442,099 A | 4/1984 | Nicolaou et al. ...... 424/248.57 |
| 4,567,290 A | 1/1986 | Nicolaou et al. ........... 560/124 |
| 4,710,521 A | 12/1987 | Soukup et al. .............. 521/118 |
| 4,759,880 A | 7/1988 | Nicolaou et al. ........... 260/413 |
| 5,087,790 A | 2/1992 | Petasis et al. ............... 585/638 |
| 5,136,501 A | 8/1992 | Silverman et al. .......... 364/408 |
| 5,177,046 A | 1/1993 | Savoca et al. .............. 502/167 |
| 5,594,732 A | 1/1997 | Bell et al. ................... 370/401 |
| 5,752,238 A | 5/1998 | Dedrick ....................... 705/14 |
| 5,756,789 A | 5/1998 | Bruce et al. ................. 556/14 |
| 5,842,040 A | 11/1998 | Hughes et al. .............. 395/831 |
| 5,845,265 A | 12/1998 | Woolston ..................... 705/37 |
| 5,870,717 A | 2/1999 | Wiecha ........................ 705/26 |
| 5,878,400 A | 3/1999 | Carter, III .................... 705/20 |
| 5,878,423 A | 3/1999 | Anderson et al. ........... 707/100 |
| 5,890,138 A | 3/1999 | Godin et al. ................. 705/26 |
| 5,896,379 A | 4/1999 | Haber ......................... 370/390 |
| 5,946,467 A | 8/1999 | Pathakis et al. ........ 395/200.66 |
| 6,030,715 A | 2/2000 | Thompson et al. ......... 428/690 |
| 6,030,917 A | 2/2000 | Weinberg et al. ........... 502/104 |
| 6,069,109 A | 5/2000 | Kao et al. .................... 502/152 |
| 6,232,467 B1 | 5/2001 | Petasis et al. ............... 544/171 |
| 6,259,699 B1 | 7/2001 | Opalka et al. .............. 370/398 |
| 6,272,474 B1 | 8/2001 | Garcia ......................... 705/37 |
| 6,336,105 B1 | 1/2002 | Conklin et al. .............. 705/80 |
| 6,336,138 B1 | 1/2002 | Caswell et al. ............. 709/223 |
| 6,377,937 B1 | 4/2002 | Paskowitz .................... 705/26 |
| 6,397,212 B1 | 5/2002 | Biffar ............................ 707/5 |
| 6,415,270 B1 | 7/2002 | Rackson et al. .............. 705/37 |
| 6,427,132 B1 | 7/2002 | Bowman-Amuah ......... 703/22 |
| 6,602,817 B1 | 8/2003 | Petasis ....................... 502/172 |
| 6,670,396 B2 * | 12/2003 | Serhan et al. ............... 514/549 |
| 2003/0236423 A1 | 12/2003 | Petasis ........................ 554/61 |

FOREIGN PATENT DOCUMENTS

| EP | 0 736 509 A2 | 10/1996 |
| EP | 0 736 509 B1 | 11/2001 |
| WO | WO 97/19415 | 5/1997 |
| WO | WO 98/19259 | 5/1998 |
| WO | WO 98/35469 | 8/1998 |
| WO | WO 99/06913 | 2/1999 |
| WO | WO 99/13417 | 3/1999 |

OTHER PUBLICATIONS

Babine, R. E. and S.L. Bender., "Molecular Recognition of Protein–Ligand Complexes: Applications to Drug Design," *Chem. Rev.* 97:1359–1472 (1997).

Bhaley, G. et al., "Solid–Phase Synthesis of Diverse Tetrahydro–1,4–Benzodiazepine–2–ones," *Tetrahedron Letters* 38(48):8375–8378 (1997).

Bläser, E. et al., "Asymmetric Steering of Oxa Diels—Alder Reactions with Silyloxydienes Employing Proline Esters as Chiral Auxiliary Groups," *Eur. J. Org. Chem.*, 329–333, (1999).

Deloux, Laurent and Morris Srebnik "Asymmetric Boron–Catalyzed Reactions", *Chem. Rev.* 93:763–784, (1993).

Durantel, et al., "Study of the Mechanism of Antiviral Action of Iminosugar Derivatives against Bovine Viral Diarrhea Virus," *J. Virology* 75(19): 8987–8998, (2001).

Du Bois, et al., "Novel, Stereoselective Synthesis of 2–Amino Saccharides," *J. Am. Chem. Soc.* 119:3179–3180, 1997.

Evans, B.E. et al., "Design of Nonpeptidal Ligands for a Peptide Receptor: Cholecystokinin Antagonists," *J. Med. Chem.* 30:1229–1239 (1987).

Fletcher, M. D. and M.C. Campbell, "Partially Modified Retro–Inverso Peptides: Development, Synthesis and Conformational Behavior," *Chem. Rev.*, 98:763–795, (1998).

Garro–Helion, et al., "Mild and Selective Palladium(0)–Catalyzed Deallylation of Allylic Amines, Allylamine and Diallylamine as Very Convenient Ammonia Equivalents for the Synthesis of Primary Amines," *J. Org. Chem.*, 58:6109–6113, (1993).

Golebiowski, A. and J. Jurczak, "α–Amino–β–hydroxy Acids in the Total Synthesis of Amino Sugars." *Synlett*, pp. 241–245, (Apr., 1993).

Guillier et al., "Linkers and Cleavage Strategies in Solid–Phase Organic Syntheis and Combinatorial Chemistry," *Chem. Rev.*, 100:2091–2157, (2000).

Hanessian, S. et al., "Design and Synthesis of Conformationally Constrained Amino Acids as Versatile Scaffolds and Peptide Manners," *Tetrahedron*, 53:12789–12854, (1997).

Hoyng, C.F. and A.D. Patel, "Aldehyde Components for Use in Four–Component Condensation ("4CC") UGI Reaction Peptide Synthesis," *Tetrahedron Lett.*, 21:4795–4798, (1980).

(Continued)

Primary Examiner—Deborah D. Carr
(74) *Attorney, Agent, or Firm*—Fish & Richardson P.C.

(57) ABSTRACT

The invention features methods for the preparation of naturally occurring trihydroxy polyunsaturated eicosanoids and their structural analogs. The invention further provides new derivatives of trihydroxy polyunsaturated eicosanoids that can be prepared according to these methods. The invention also provides trihydroxy polyunsaturated eicosanoids and their use in pharmaceutical compositions.

9 Claims, No Drawings

OTHER PUBLICATIONS

Humphrey, J.M. and A.R. Chamberlin, "Chemical Synthesis of Natural Product Peptides: Coupling Methods for the Incorporation of Noncoded Amino Acids into Peptides," *Chem. Rev.,* 97:2243–2266, (1997).

König et al., "Synthesis of N–tert–Alkylglyoxylic Acid Amides," *Synthesis,* pp. 1233–1234, (1993) [in German, English language abstract on 1$^{st}$ page of article].

Marx et al., "Synthetic Design for Combinatorial Chemistry. Solution and Polymer–Supported Synthesis of Polycyclic Lactams by Intramolecular Cyclization of Azomethine Ylides," *J. Am. Chem. Soc.,* 119:6153–6167, (1997).

Mehta et al., "Structure–Activity Relationship of a New Class of Anti–Hepatitis B Virus Agents," *Antimicrobial Agents and Chemotherapy,* 46(12):4004–4008 (2002).

Nicolaou, et al., "Novel IBX–Mediated Process for the Synthesis of Amino Sugars and Libraries Thereof," *Angew. Chem. Int. Ed. Engl.,* 39:2525–2529, (2000).

Nicolaou, et al., "Lipoxins and Related Eicosanoids: Biosynthesis, Biological Properties, and Chemical Synthesis," *Angew. Chem. Int. Ed. Engl.* 30:1100–1116, (1991).

Noyori, R. (Ed.), "Enantioselective Addition of Organometallic Reagents to Carbonyl Compounds: Chirality Transfer, Multiplication, and Amplification," Chapter 5 in *Asymmetrical Catalysis in Organic Synthesis*, New York: John Wiley & Sons, Inc., pp. 255–297 (1994).

Nugent, William A., "Chiral Lewis Acid Catalysis. Enantioselective Addition of Azide to Meso Epoxides", *J. Am. Chem. Soc.,* 114(7):2768–2769 (1992).

O'Donnell, Martin J. and J. Falmagne, "The Synthesis of Amino Acids via Organoboranes." *J. Chem. Soc. Chem. Commun.,* No. 17, pp. 1168–1169, (Sep. 1, 1985).

Petasis, N. A. and I.A. Zavialov, "The Boronic Acid Mannich Reaction: A New Method for the Synthesis of Geometrically Pure Allylamines," *Tetrahedron Letters,* 34(4):583–586, (1993).

Petasis, N.A. and I.A. Zavialov, "A New and Practical Synthesis of α–Amino Acids from Alkenyl Boronic Acids," *J. Am. Chem. Soc.,* 119(2):445–446, (1997).

"Scope and Editorial Policy," *Organometallics,* published by the American Chemical Society 21(1):13A, 14A (2002).

Serhan et al., "Novel Functional Sets of Lipid–derived Mediators with Antiinflammatory Actions Generated from Omega–3 Fatty Acids via Cyclooxygenase 2–Nonsteroidal Antiinflammatory Drugs and Transcellular Processing, " *J. Exp. Med.* 192:1197–1204, (2000).

Thompson, L.A. and J.A. Ellman, "Synthesis and Applications of Small Molecule Libraries," *Chem. Rev.* 96:555–600 (1996).

Waki, M. and J. Meienhofer, "Peptide Synthesis Using the Four–Component Condensation (Ugi Reaction)," *J. Am. Chem. Soc.,* 99:6075–6082, (1977).

Yamamoto, Y. and N. Asao, "Selective Reactions Using Allylic Metals," *Chem. Rev.,* 93:2207–2293, (1993).

* cited by examiner

TRIHYDROXY POLYUNSATURATED EICOSANOIDS

CROSS REFERENCE TO RELATED APPLICATIONS

This application is a continuation-in-part of and this application claims the benefit of U.S. Provisional Application No. 60/369,543, filed on Apr. 1, 2002, which is incorporated herein by reference in its entirety.

STATEMENT REGARDING FEDERALLY SPONSORED RESEARCH

The U.S. Government may have certain rights in this invention pursuant to Grant No. PO1-DE13499 (Subcontract) awarded by the National Institutes of Health.

BACKGROUND

This invention relates to trihydroxy polyunsaturated eicosanoid derivatives and methods for the preparation of such compounds and their structural analogs.

The conversion of arachidonic acid (C20:4) to a variety of bioactive eicosanoids, including prostaglandins (PG), leukotrienes (LT) and lipoxins (LX) is well known (Nicolaou, K. C.; Ramphal, J. Y.; Petasis, N. A.; Serhan, C. N. *Angew. Chem. Int. Ed. Engl.* 1991, 30, 1100).

It was recently reported that endothelial cells upregulated with COX-2 and treated with aspirin, convert eicosapentaenoic acid to a new series of hydroxylated polyunsaturated eicosanoids (Serhan, C. N. etal. *J. Exp. Med.* 2000. 192, 1197). The present invention provides methods for preparing such lipid mediators, which have potential use in the development of new pharmaceuticals.

It has been suggested that dietary ω-3 polyunsaturated fatty acids (PUFA) (De Caterina, R., Endres, S.; Kristensen, S. D.; Schmidt, E. B., (eds). *ω-3 Fatty Acids and Vascular Disease*, Springer-Verlag, London. 166 pp. 1993) have beneficial effects in human health and in the prevention of various diseases, including inflammation, cancer (Iigo, M. et al, *Br. J. Cancer,* 1997, 75, 650) and cardio-vascular diseases (Billman, G. E., et al. *Circulation.* 1999, 99, 2452). Eicosapentaenoic acid (C20:5), the major PUFA in fish oil, was shown to form prostaglandins (PG), leukotrienes (LT) and other eicosanoids that are similar to those derived from arachidonic acid (C20:4). The different biological properties of these molecules were considered to be responsible for the role of PUFA. Despite numerous studies in this area, however, the molecular mechanisms for the actions of PUFA remain unknown.

It was recently demonstrated (Serhan, C. N. et al. *J. Exp. Med.* 2000. 192, 1197) that human endothelial cells with upregulated COX-2 treated with aspirin convert ω-3 polyunsaturated fatty acids to 18R-HEPE as well as 15R-HEPE. While 15R-HEPE led to the 5-series lipoxins (15R-LXA$_5$), 18R-HEPE led to 5S,12R,18R-triHEPE (1), a novel trihydroxy-eicosanoid related to the structure of LTB$_4$. In a more recent publication compounds of this type were named Resolvins (Serhan, C. N.; et al, *J. Exp. Med.* 2002, 196, 1025).

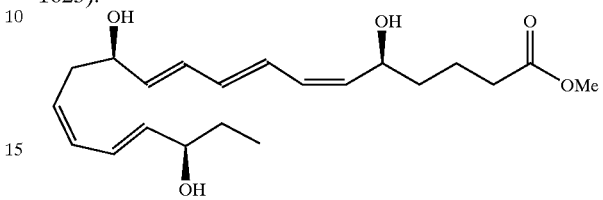

5S, 12R, 18R-triHEPE (1)

The formation of these trihydroxy polyunsaturated eicosanoids from PUFA suggests a novel mechanism for the therapeutic benefits of PUFA with major implications for new therapeutic approaches to a variety of diseases. Methods for the preparation of such compounds, therefore, are of great importance to the development of new therapeutic agents. Furthermore, the development of structural derivatives of these compounds may be useful for the optimization of their pharmacological profile and other desirable drug-like properties.

SUMMARY

The invention features methods for the preparation of naturally occurring trihydroxy polyunsaturated eicosanoids and their structural analogs. The invention further provides new derivatives of trihydroxy polyunsaturated eicosanoids that can be prepared according to these methods.

In general, in one aspect, the invention features methods of preparing trihydroxy polyunsaturated eicosanoids, such as 1, as outlined in Scheme 1. The two (Z) C=C bonds can be formed via selective hydrogenation, such as Lindlar hydrogenation, of bis-alkynyl precursor 2. Compound 2 can be prepared via a palladium-mediated coupling (coupling step a) between intermediates 3 and 4, where X is Br, or I. Compound 4 can be prepared via the alkenylation of aldehyde 5, which is readily available from protected epoxide 6. Intermediate 3 can be prepared in several different ways, as discussed below, from precursors 7 and 8, while compound 8 can readily prepared from protected epoxide 9.

Scheme 1

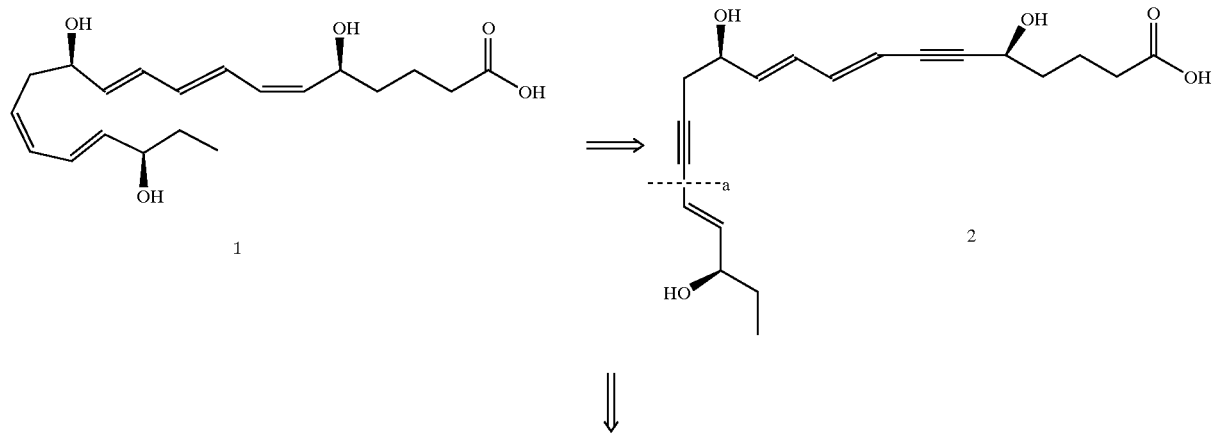

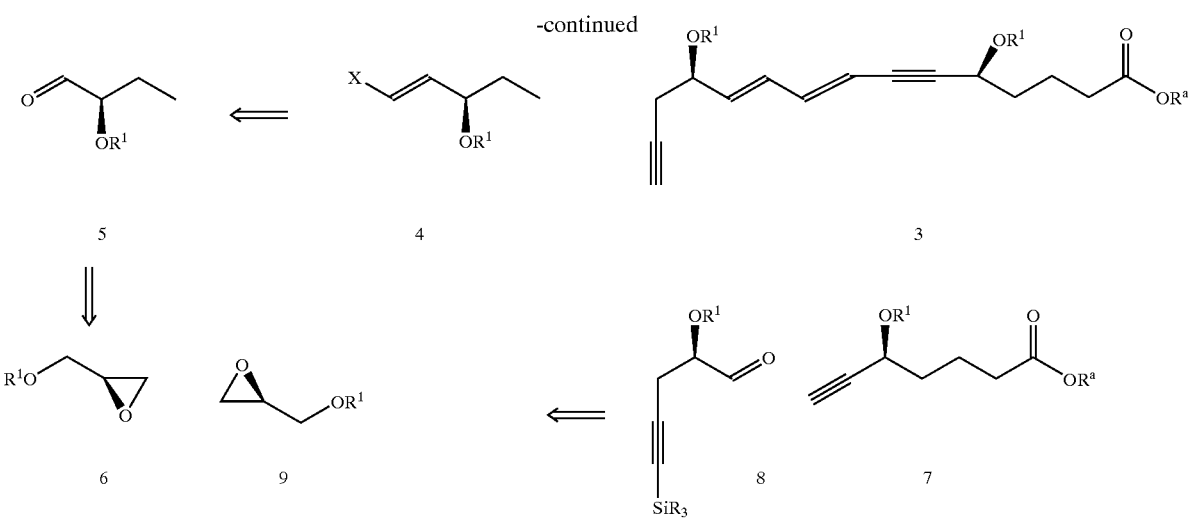
The intermediate 3 can be prepared in several different ways, as outlined in Scheme 2.
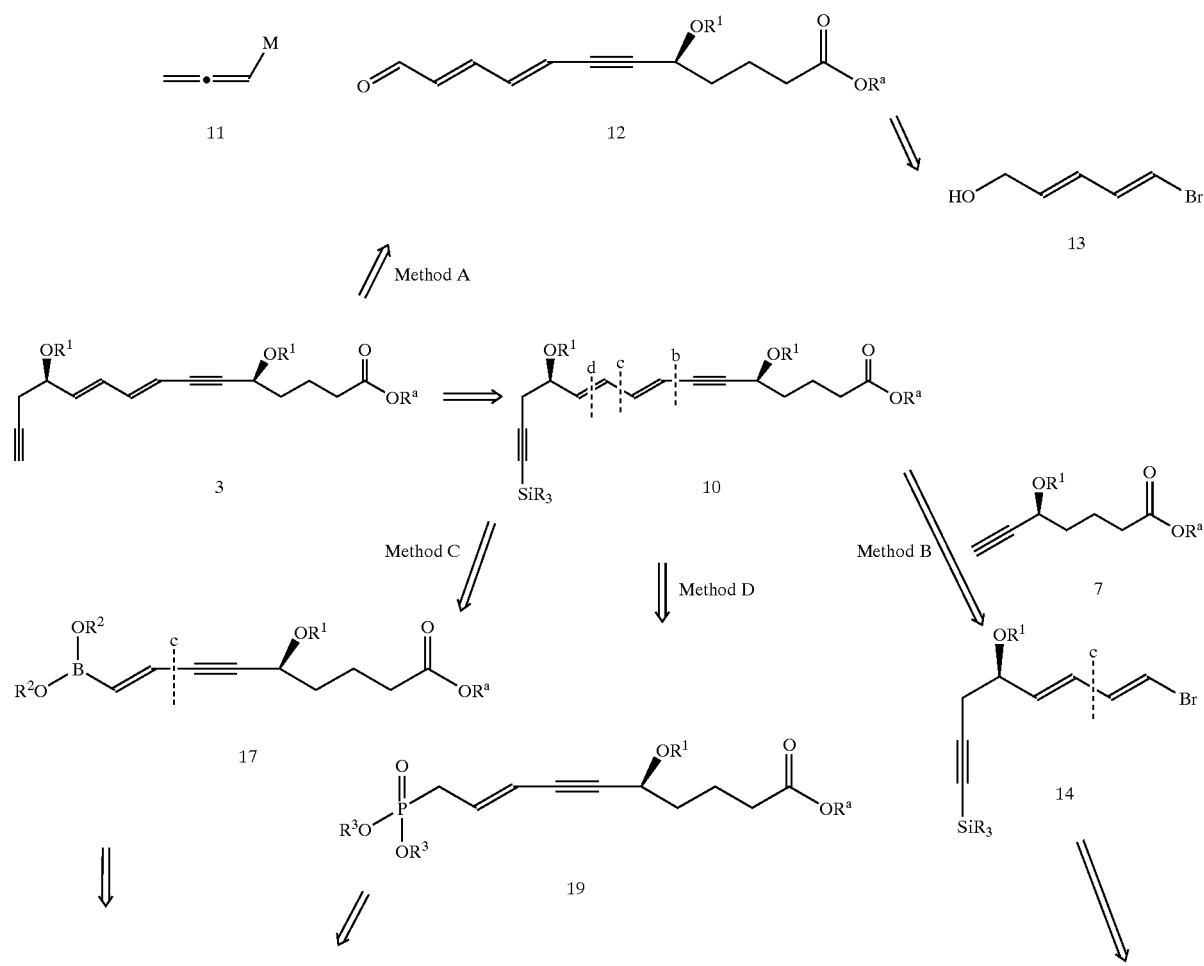

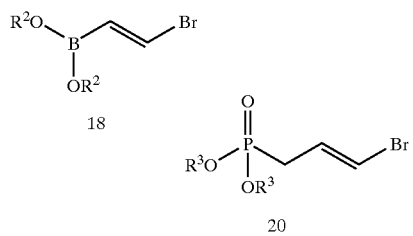
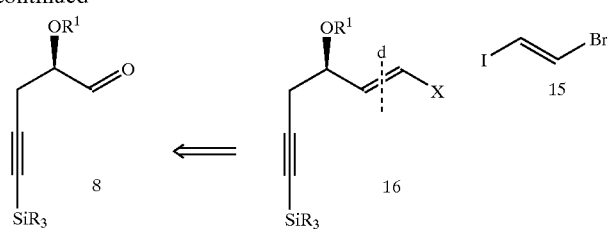

According to Method A, compound 3 can be prepared via the addition of an allenyl reagent 11 (M is magnesium, zinc, copper, tin, silicon or boron) to precursor 12, which is readily available via the Pd-coupling between the known bromide 13 and the known alkyne 7. According to Method B, compound 3 is prepared from precursor 10, which is produced via Pd-mediated coupling (coupling process b) of 7 with intermediate 14. Compound 14, can be prepared via Pd-coupling (coupling process c) between 15 and precursor 16, which can be prepared via the alkenylation (coupling process d) of aldehyde intermediate 8. According to Method C, precursor 10, is formed via the Pd-coupling (coupling process c) between 16 and alkenyl boron compound 17, which is readily available via the Pd-coupling (coupling process c) between alkenyl boron compound 18 and intermediate 7. Finally, according to Method D, compound 10, is prepared via the alkenylation (coupling process d) of aldehyde intermediate 8 with phosphonate intermediate 19, which is readily available via the Pd-coupling (coupling process b) between the compound 20 with 7.

The invention also provides synthetic analogs of trihydroxy polyunsaturated eicosanoids that may exhibit improved chemical and biological properties. These include the compounds shown in Scheme 3, having the general formulas 21–24.

Scheme 3

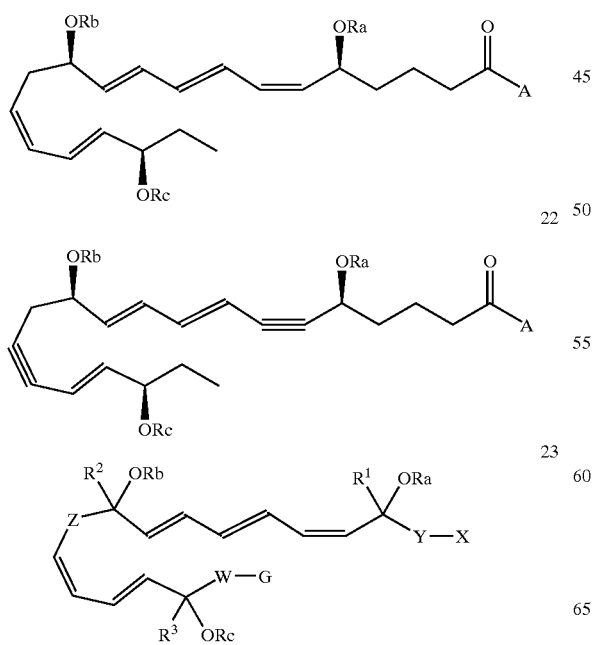

wherein,

A is hydroxy, alcoxy, aryloxy, amino, alkylamino, dialkylamino,or —OM, where M is a cation selected from a group consisting of ammonium, tetra-alkyl ammonium, Na, K, Mg, or Zn;

Ra, Rb and Rc, are independently selected from a group that consists of hydrogen, alkyl, aryl, heteroaryl, acyl, silyl, alcoxyacyl or aminoacyl;

$R^1$, $R^2$ and $R^3$ are independently selected from a group that consists of hydrogen, alkyl, aryl or heteroaryl;

X is selected from a group that consists of:
—C(O)-A, —SO2-A, —PO(OR)-A, where A is hydroxy, alcoxy, aryloxy, amino, alkylamino, dialkylamino, or —OM, where M is a cation selected from a group consisting of ammonium, tetra-alkyl ammonium, Na, K, Mg, or Zn; and R is hydroxyl or alcoxy;

Y, Z and W are linkers selected from a group consisting of a ring or a chain of up to 20 atoms that may include one or more nitrogen, oxygen, sulfur or phosphorous atoms, provided that linker A can have one or more substituents selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that the linker may also contain one or more fused rings, including carbocyclic, heterocyclic, aryl or heteroaryl rins, provided that all linkers Y are connected to the adjacent C(R)OR group via a carbon atom;

G is selected from a group that consists of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido.

In other aspects, the invention also features pharmaceutical compositions including the compounds of the invention, as well as therapeutic uses for such compounds and compositions in treating and/or preventing a disease or condition associated with inflammation or inflammatory response, or abnormal cell proliferation.

The details of one or more embodiments of the invention are set forth in the description below. Unless otherwise defined, all technical and scientific terms used herein have the meaning commonly understood by one of ordinary skill in the art to which this invention belongs. All publications, patent applications, patents, and other references mentioned herein are incorporated by reference in their entirety. In case of conflict, the present specification, including definitions, will control. Other features and advantages of the invention will become apparent from the description and the claims.

DETAILED DESCRIPTION

Definitions:

As used in this specification, alkyl groups can include straight-chained, branched and cyclic alkyl radicals containing up to about 20 carbons. Suitable alkyl groups may be saturated or unsaturated. Further, an alkyl may also be substituted one or more times on one or more carbons with substituents selected from the group consisting of C1–C6 alkyl, C3–C6 heterocycle, aryl, halo, hydroxy, amino, alkoxy and sulfonyl. Additionally, an alkyl group may contain up to 10 heteroatoms or heteroatom substituents. Suitable heteroatoms include nitrogen, oxygen, sulfur and phosphorous.

As used in this specification, aryl groups are aryl radicals which may contain up to 10 heteroatoms. An aryl group may also be optionally substituted one or more times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that the ring may also contain one or more fused rings, including carbocyclic, heterocyclic, aryl or heteroaryl rings.

Methods for Preparing Trihydroxy Polyunsaturated Eicosanoids and Analogs

In general, in one aspect, the invention features methods of preparing trihydroxy polyunsaturated eicosanoids, such as 1, as outlined in Scheme 1. The two (Z) C=C bonds can be formed via selective hydrogenation, such as Lindlar hydrogenation, of bis-alkynyl precursor 2. Compound 2 can be prepared via a palladium-mediated coupling (coupling step a) between intermediates 3 and 4, where X is Br, or I. Compound 4 can be prepared via the alkenylation of aldehyde 5, which is readily available from protected epoxide 6. Intermediate 3 can be prepared in several different ways, as discussed below, from precursors 7 and 8, while compound 8 can readily prepared from protected epoxide 9.

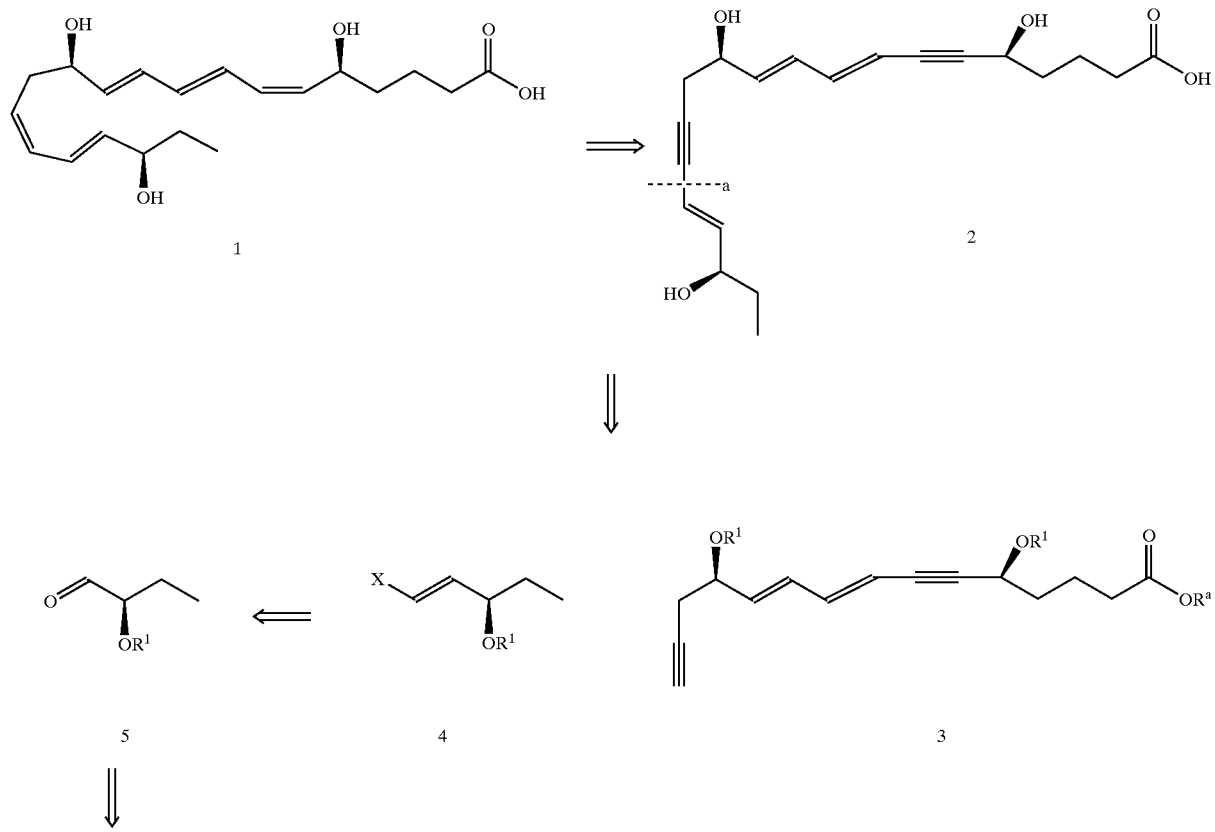

Scheme 1

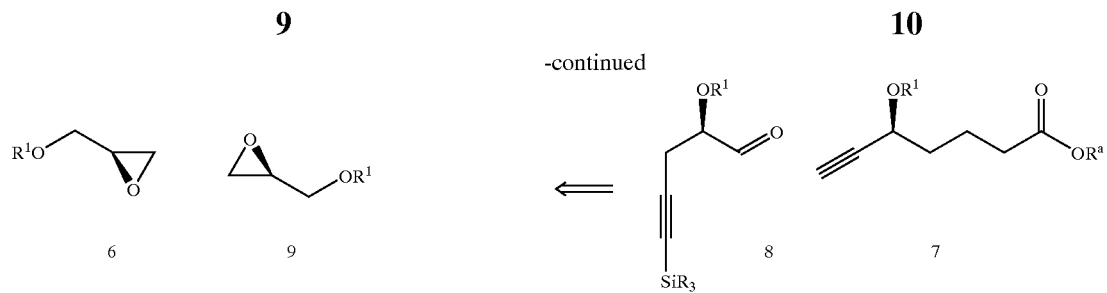
The intermediate 3 can be prepared in several different ways, as outlined in Scheme 2.
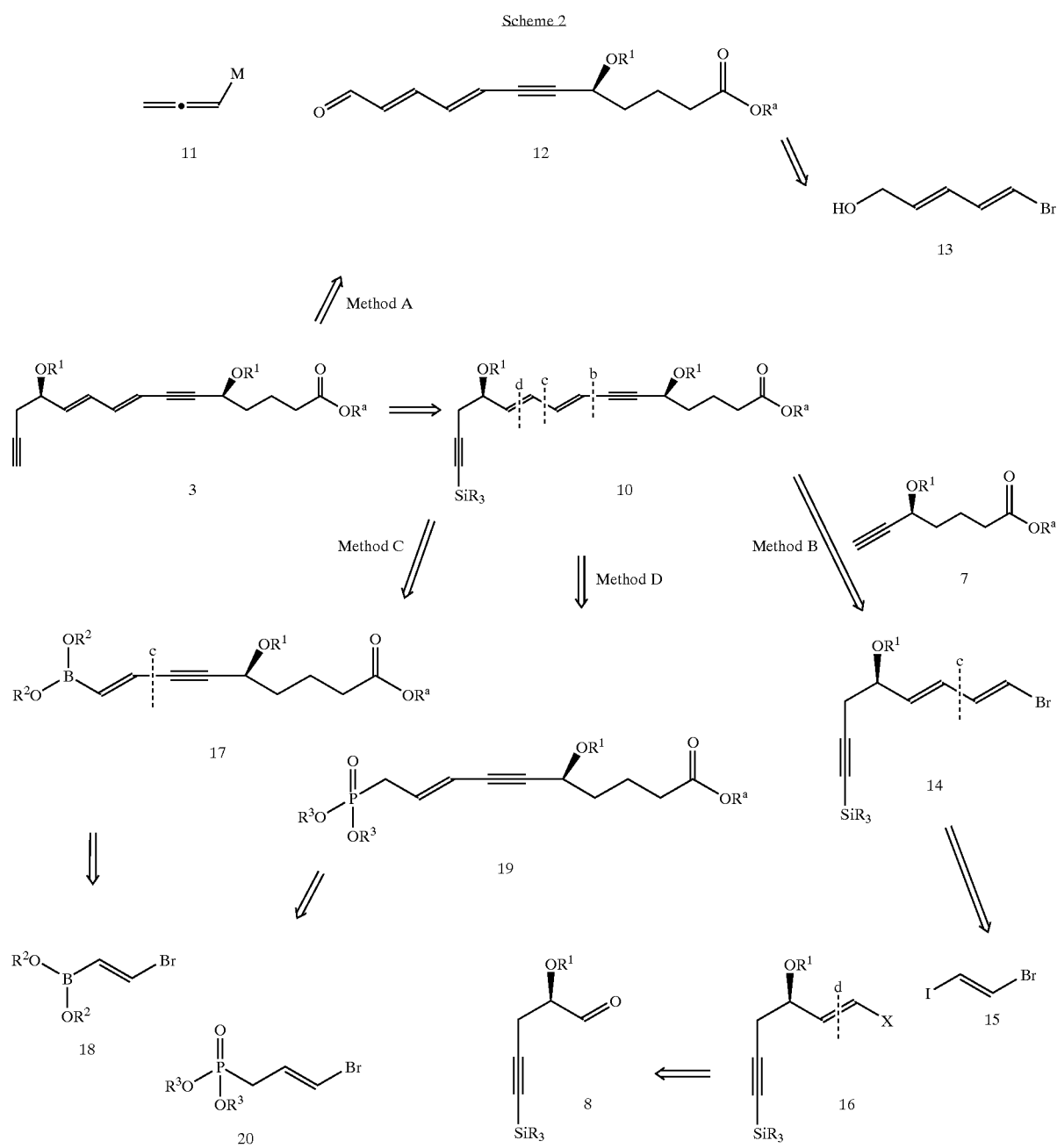

According to Method A, compound 3 can be prepared via the addition of an allenyl reagent 11 (M is magnesium, zinc, copper, tin, silicon or boron) to precursor 12, which is readily available via the Pd-coupling between the known bromide 13 and the known alkyne 7. According to Method B, compound 3 is prepared from precursor 10, which is produced via Pd-mediated coupling (coupling process b) of 7 with intermediate 14. Compound 14, can be prepared via Pd-coupling (coupling process c) between 15 and precursor 16, which can be prepared via the alkenylation (coupling process d) of aldehyde intermediate 8. According to Method C, precursor 10, is formed via the Pd-coupling (coupling process c) between 16 and alkenyl boron compound 17, which is readily available via the Pd-coupling (coupling process c) between alkenyl boron compound 18 and intermediate 7. Finally, according to Method D, compound 10, is prepared via the alkenylation (coupling process d) of aldehyde intermediate 8 with phosphonate intermediate 19, which is readily available via the Pd-coupling (coupling process b) between the compound 20 with 7.

This strategy is highly convergent and the two Z double bonds can be generated at the last step and thereby enhancing the stability of the product. The present invention involves several dinstinct building blocks which can be readily prepared as described below.

Scheme 4 shows the synthesis of building blocks of type 4, while Scheme 5 show the synthesis of building blocks of type 8 and 16. In both cases the stereochemistry of these building blocks is established unambiguously from the starting glycidol and it is retained throughout the synthesis, allowing the synthesis of products with high stereochemical purity.

Scheme 4

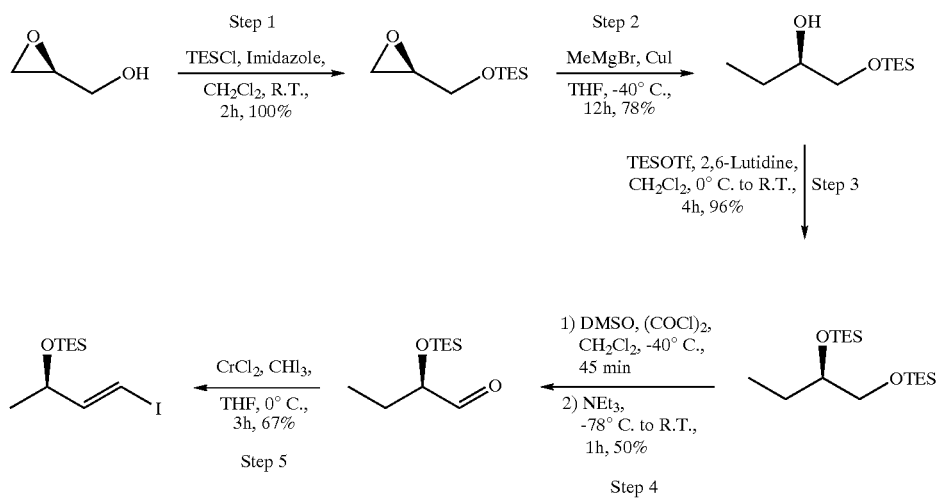

Scheme 5

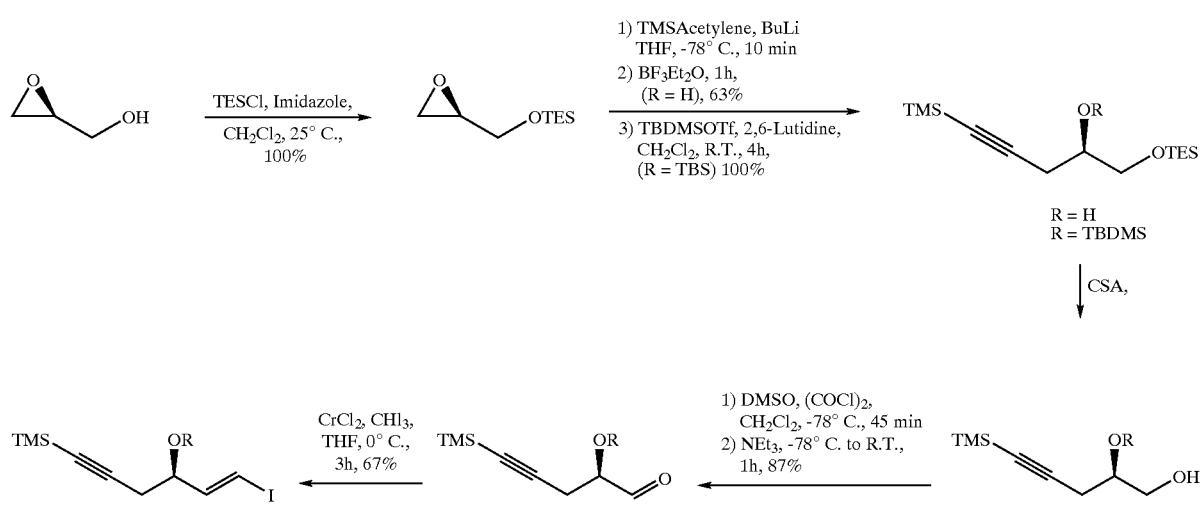

Scheme 6 shows a practical synthesis of intermediate of type 7 with high stereochemical purity.

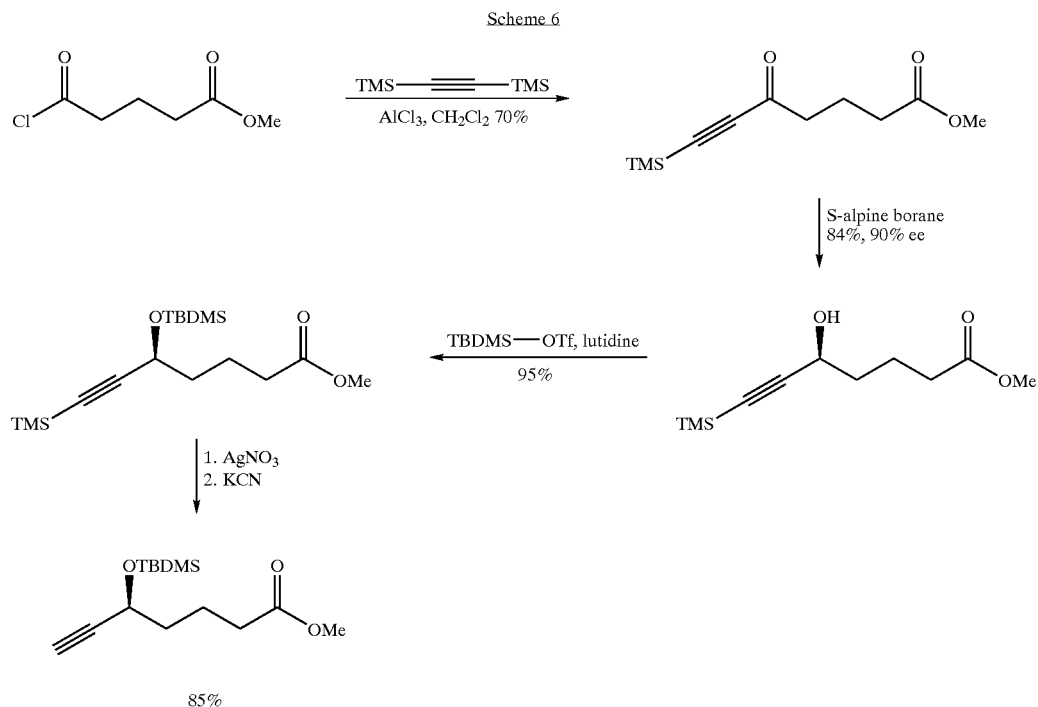

The combination of these building blocks can be done in a variety of ways. According to Method A (Scheme 2), the alkyne intermediate of type 7, can be coupled with a dienyl bromide-alcohol to give a product that can be oxidized to an aldehyde. Addition of allenyl boronic acid derivative, according to chemistry reported by Yamamoto (Ikeda, N.; Arai, I.; Yamamoto, H. *J. Am. Chem. Soc.* 1986, 108, 483.) forms the intermediate of type 3, in good overall yield, but with modest stereocontrol.

Scheme 8 shows an alternative way to prepare the intermediate of type 3 is via an intermediate of type 10. According to Method 3 (Scheme 2) Negishi-type coupling of intermediate of type 16 followed by Sonogashira coupling with intgermediate of type 7 gives the intermediate of type 10, which can be desilylated to form the key intermediate of type 3.

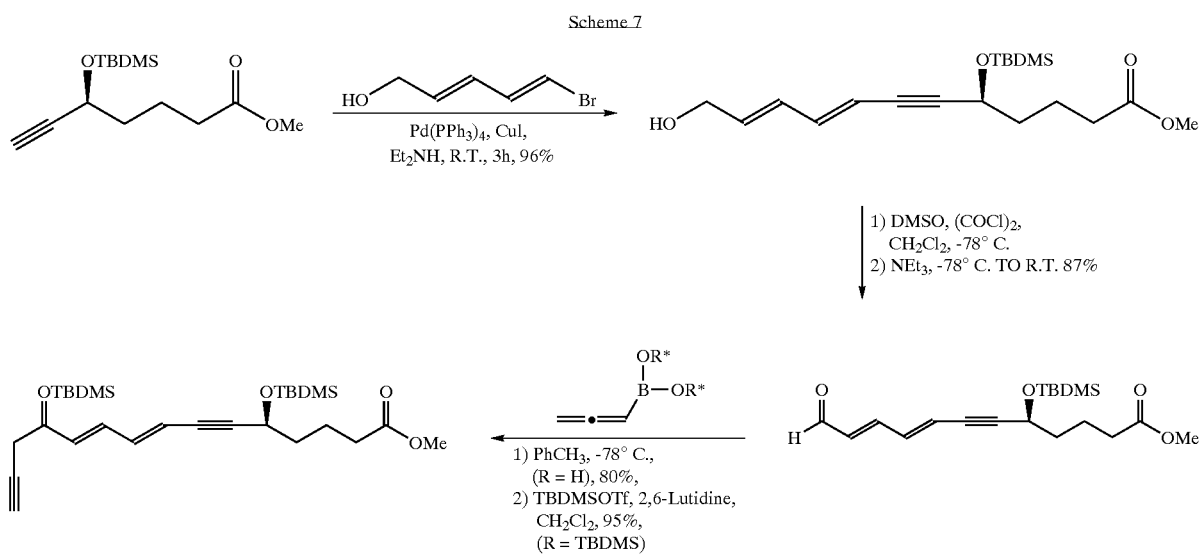

Scheme 8

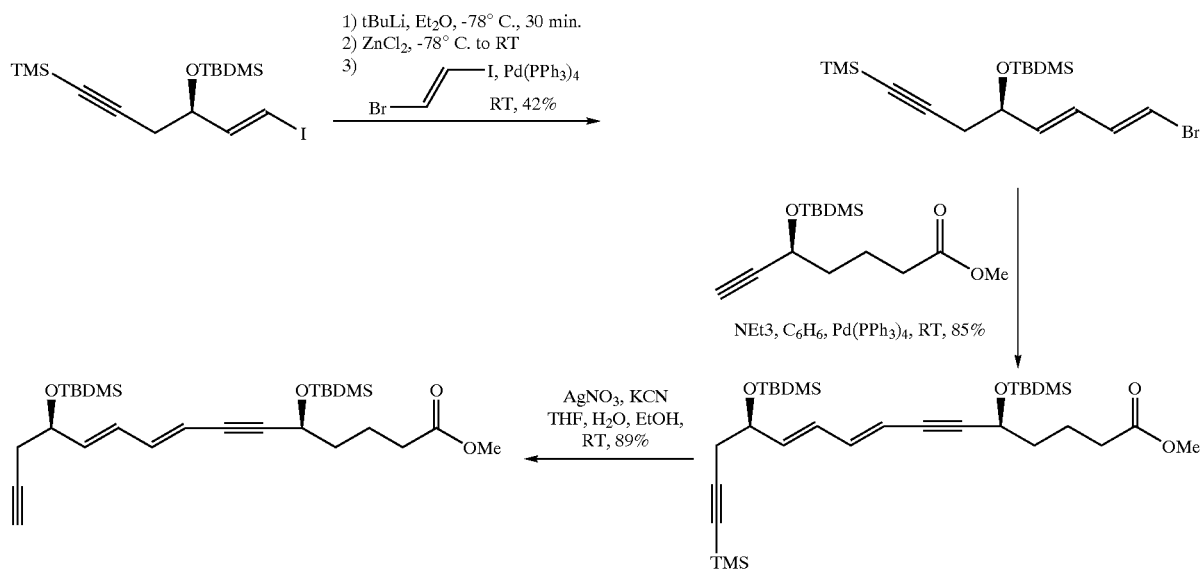

Another approach according to Method C is shown in Scheme 9. Sonogashira coupling, followed by a Suzuki coupling gives the final product. This iterative coupling can be done in a sequential manner and it is possible to do this in one pot.

Scheme 10 shows one of the most effective ways to make intermediates of type 3. It is based on a Wittig-type coupling among a readily available intermediate phosphonate and a similar aldehyde intermediate.

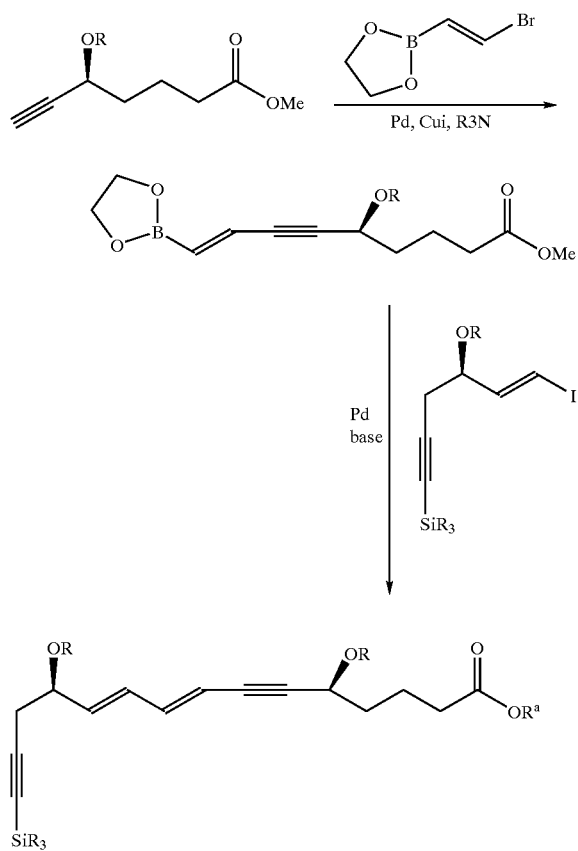

Scheme 9

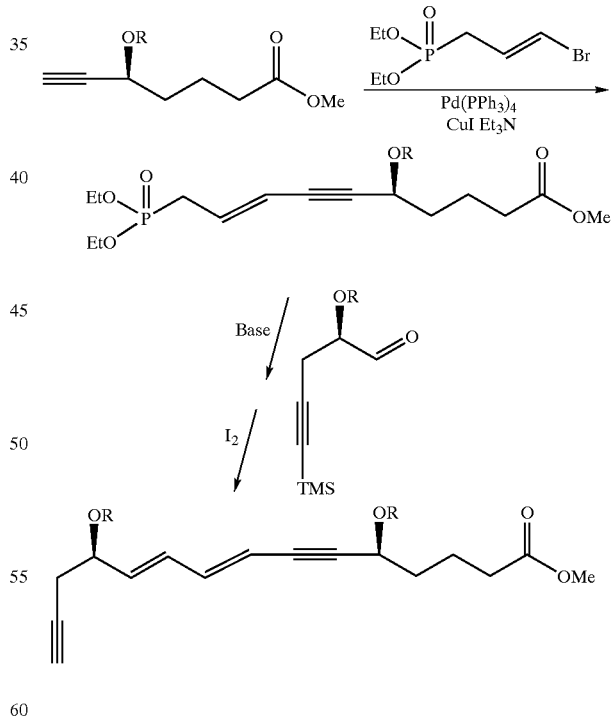

Scheme 10

The final assembly of these molecules can be done as shown in Scheme 11. Sonogashira coupling of the two key intermediates, followed by deprotection gives the bis-alkynyl product of type 2. The final compound of type 1 is then obtained via selective hydrogenation using Lindlar catalyst.

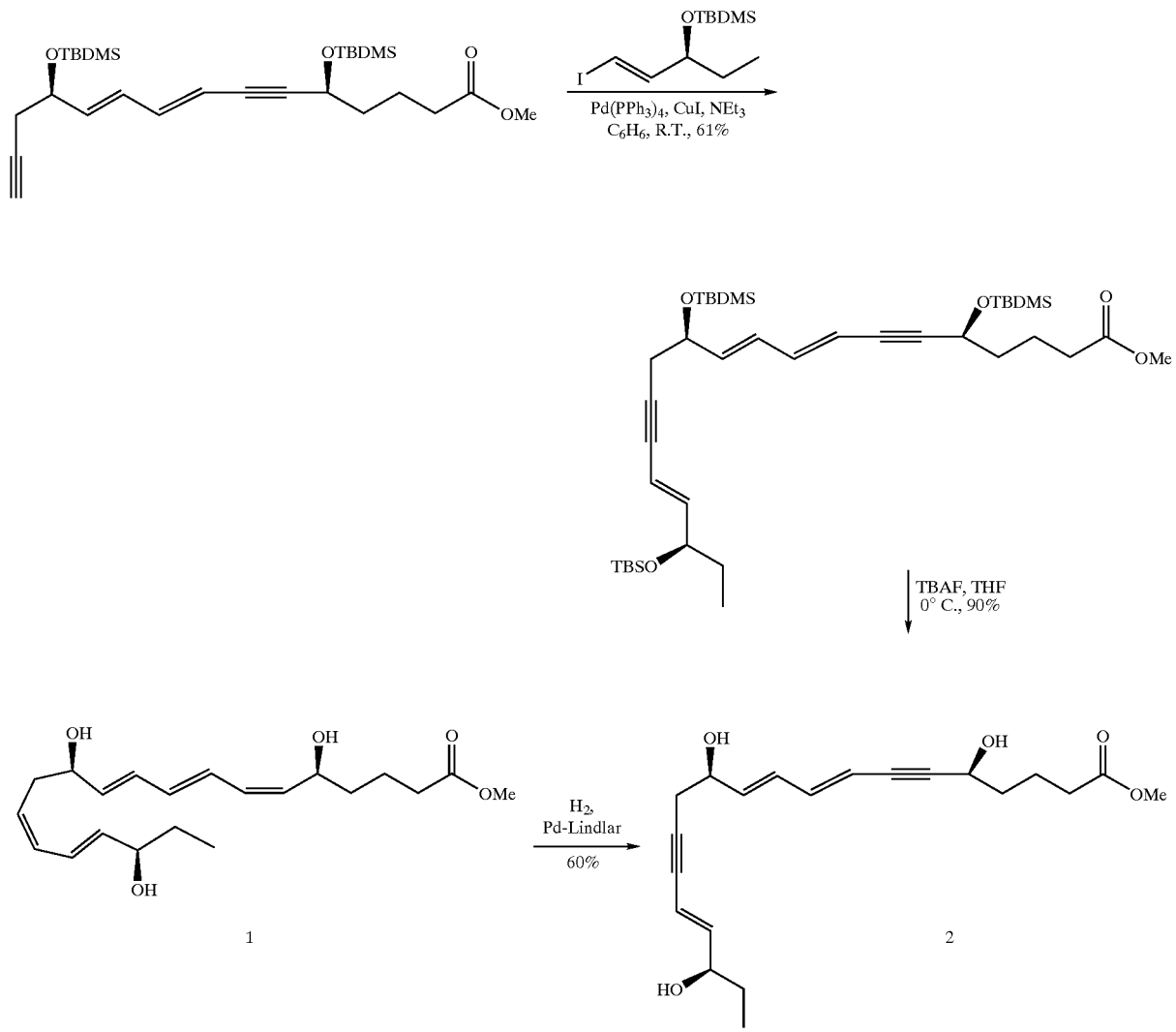

Scheme 9

Overall the synthetic methodology described herein is highly convergent and allows a number of possible combinations of the key intermediates by using Pd-mediated coupling processes.

The above methodology is highly versatile and it can be readily extended to analogs of Trihydroxy Polyunsaturated Eicosanoids that have similar frameworks.

Trihydroxy Polyunsaturated Eicosanoid Analogs

In another aspect, the invention provides non-naturally occurring structural analogs of trihydroxy polyunsaturated eicosanoids that can be prepared according to the methods described above. The synthetic polyunsaturated eicosanoids may exhibit improved chemical and biological properties. These include the compounds shown in Scheme 3, having the general formulas 21–24.

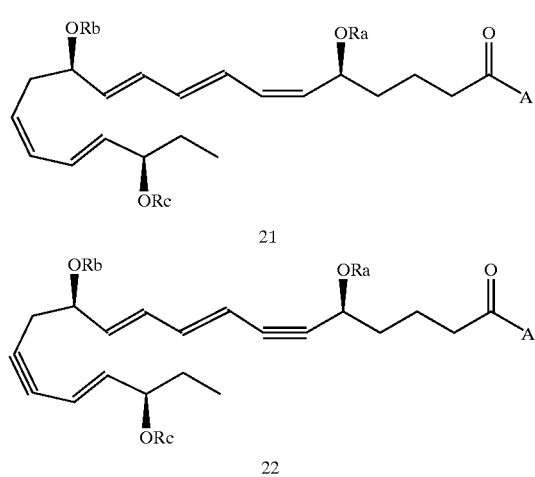

Scheme 3

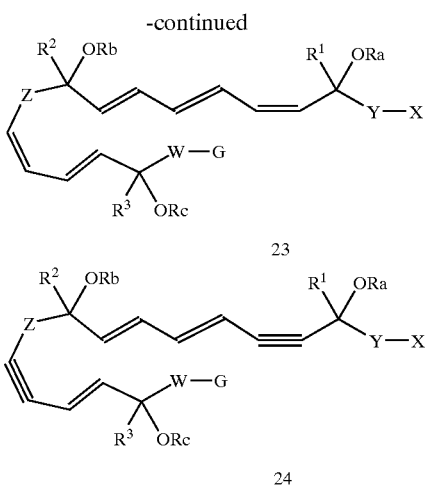

wherein,

A is hydroxy, alcoxy, aryloxy, amino, alkylamino, dialkylamino, or —OM, where M is a cation selected from a group consisting of ammonium, tetra-alkyl ammonium, Na, K, Mg, or Zn;

Ra, Rb and Rc, are independently selected from a group that consists of hydrogen, alkyl, aryl, heteroaryl, acyl, silyl, alcoxyacyl or aminoacyl;

$R^1$, $R^2$ and $R^3$ are independently selected from a group that consists of hydrogen, alkyl, aryl or heteroaryl;

X is selected from a group that consists of:
—C(O)-A, —SO2-A, —PO(OR)-A, where A is hydroxy, alcoxy, aryloxy, amino, alkylamino, dialkylamino, or —OM, where M is a cation selected from a group consisting of ammonium, tetra-alkyl ammonium, Na, K, Mg, or Zn; and R is hydroxyl or alcoxy;

Y, Z and W are linkers selected from a group consisting of a ring or a chain of up to 20 atoms that may include one or more nitrogen, oxygen, sulfur or phosphorous atoms, provided that linker A can have one or more substituents selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that the linker may also contain one or more fused rings, including carbocyclic, heterocyclic, aryl or heteroaryl rins, provided that all linkers Y are connected to the adjacent C(R)OR group via a carbon atom;

G is selected from a group that consists of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido.

Pharmaceutical Compositions

The compounds of the invention can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the treatment methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Therapeutic Uses

The compounds of the invention are structural analogs of naturally-occurring trihydroxy polyunsaturated eicosanoids that are known to have biological activity against a wide variety of targets, including diseases or conditions associated with inflammation or inflammatory response, undesired cell proliferation, such as cancer, and cardiovascular diseases. As such, the compounds of the invention are expected to have similar activity against those targets.

Accordingly, in one aspect the invention features methods of ameliorating or treating diseases or conditions associated with inflammation or inflammatory response, involving the administration to a subject of a therapeutically effective amount of a compound or compounds of the invention, such that inflammation or an inflammatory response are significantly reduced or eliminated in the subject. A significant reduction includes the reduction or elimination of a symptom or symptoms associated with the inflammation or inflammatory response.

In another aspect, the invention features methods of ameliorating or treating diseases or conditions associated with undesired cell proliferation, such as cancer, involving the administration to a subject of an effective amount of a compound or compounds of the invention. In general, an effective amount is an amount sufficient to ensure adequate exposure of a target cell population, such that abnormal cell proliferation is substantially slowed or halted. A target population is a population of cells undergoing abnormal cell proliferation, such as cancerous and/or tumorous growth.

The invention will be further described in the following examples, which are illustrative only, and which are not intended to limit the scope of the invention described in the claims.

EXAMPLES

The invention will be further described in the following examples, which are illustrative only, and which are not intended to limit the scope of the invention described in the claims.

In the following examples, efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric. Starting materials used in these examples are generally either commercially available or can be readily prepared from commercially available reagents by a procedure involving one or more steps.

Example 1

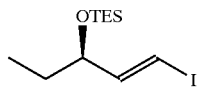

Step 1: To a solution of (R)-glycidol (4.0 g, 54 mmol) in CH$_2$Cl$_2$ (54 ml) at 0° C. were added imidazole (4.78 g, 70.19 mmol), DMAP (330 mg, 2.7 mmol) and then by canula a solution of triehylsilyl chloride (9.06 ml, 54 mmol) in CH$_2$Cl$_2$ (10 ml). The reaction was warmed to room temperature and stirred for 2 hours. The resulting white slurry mixture was quenched with water and the product was extracted with ether, washed with brine, dried and concentrated. Flash column chromatography (silica gel, 5% ethyl acetate/hexanes) afforded the pure product as a colorless liquid in quantitative yield. $^1$H NMR (250 MHz, CDCl$_3$): δ 3.79 (dd, J=11.6, J'=2.9 Hz, 1H), 3.76 (dd, J=11.8, J'=5.1 Hz, 1H), 3.02 (m, 1H), 2.69 (dd, J=5.2 Hz, J'=4.2 Hz, 1H), 2.55 (dd, J=5.1 Hz, J'=2.6 Hz, 1H), 0.90 (t, J=8.1 Hz, 9H), 0.55 (q, J=8.0 Hz, 6H). $^{13}$C NMR (62 MHz, CDCl$_3$): δ 63.580, 52.371, 44.582, 6.634, 4.317.

Step 2: To a suspension of CuI (834 mg, 4.39 mmol) in THF (100 ml) was added dropwise a 3.0 M solution of MeMgBr (14.6 ml, 43.88 mmol) at −10° C. The resulting mixture was then cooled to −40° C. and a solution of triethylsilyl protected glycidol (2.75 g, 14.63 mmol) in THF (10 ml) was added by a canula and the resulting solution was stirred overnight. Reaction mixture was then quenched with saturated NH$_4$Cl, extracted with ether, washed with brine, dried and concentrated. Flash column chromatography (silica gel, 10% ethyl acetate/hexanes) afforded the pure product as a colorless liquid in 78% yield. $^1$H NMR (250 MHz, CDCl$_3$): δ 3.59 (dd, J=9.4 Hz, J'=3.3 Hz, 1H), 3.53 (m, 1H), 3.35 (dd, J=9.4 Hz, J'=7.2 Hz, 1H), 2.45 (broad s, 1H), 1.41 (q, J=7.2 Hz, 2H), 0.93 (t, J=7.4 Hz, 12H), 0.58 (q, J=7.2 Hz, 6H). $^{13}$C NMR (62 MHz, CDCl$_3$): δ 73.213, 66.580, 25.498, 9.809, 6.498, 4.278.

Step 3: To a solution of product from Step 2 (2.20 g, 10.78 mmol) in CH$_2$Cl$_2$ (40 ml) were added dropwise at 0° C. 2,6-Lutidine (2.8 ml, 23.7 mmol) and triethylsilyloxy triflate (3.6 ml, 16.17 mmol). The reaction mixture was warmed up to room temperature and stirred for 4 hours. The solution was then poured into a solution of saturated NH$_4$Cl and extracted with diethyl ether. The combined extracts were dried and concentrated. Flash column chromatography (silica gel, 5% ethyl acetate/hexanes) afforded the pure product in quantitative yield. $^1$H NMR (250 MHz, CDCl$_3$): δ 3.59 (m, 1H), 3.49 (dd, J=9.6 Hz, J'=5.4 Hz, 1H), 3.39 (dd, J=9.7 Hz, J'=6.6 Hz, 1H), 1.58 (m, 1H), 0.94 (t, J=7.4 Hz, 9H), 0.93 (t, J=7.4 Hz, 9H), 0.88 (t, 7.2 Hz, 3H), 0.61 (q, J=7.0 Hz, 6H), 0.58 (q, J=7.0 Hz, 6H). $^{13}$C NMR (62 MHz, CDCl$_3$): δ 74.296, 66.562, 26.872, 9.530, 6.881, 6.747, 5.008, 4.335.

Step 4: A 2.0 M solution of oxalyl chloride in dichloromethane (16.1 ml, 32 mmol) was added dropwise at −78° C. to a solution of DMSO (4.56 ml, 64 mmol) in dichloromethane (30 ml). The reaction was stirred for 15 minutes at −78° C. and then a solution of product of Step 3 (2.33 g, 7.3 mmol) in dichloromethane (20 ml) was added through a canula. Stirring was continued for one hour at −78° C. followed by 45 minutes at −40° C. The solution was then cooled again at −78° C. and treated with triethylamine (15.2 ml, 109 mmol). The reaction mixture was allowed to warm to room temperature and then it was quenched with water and the product was extracted with ether, washed with brine, dried and concentrated. Flash column chromatography (silica gel, 5% ethyl acetate/hexanes) afforded the product as a colorless liquid in 50% yield. $^1$H NMR (360 MHz, CDCl$_3$): δ 9.56 (s, 1H), 3.87 (1H), 1.63 (2H), 0.94 (t, 9H), 0.91 (t, 3H), 0.59 (q, 6H). $^{13}$C NMR (90 MHz, CDCl$_3$) δ 204.440, 78.458, 25.767, 8.968, 6.501, 4.714.

Step 5: To a suspension of anhydrous CrCl$_2$ (1.456 g, 11.85 mmol) in THF (10 ml) was added at 0° C. a solution of iodoform (1.575 g, 4.0 mmol) in THF (6 ml) and a solution of the aldehyde from Step 4 (280 mg, 1.48 mmol) in THF (6 ml) by a double-tipped needle. The resulting mixture was stirred for 2 hours at 0° C. and for 1 hours at room temperature. It was then poured into water, extracted with ethyl acetate and washed with brine. The combined extracts were dried and concentrated. Flash column chromatography (silica gel, hexanes) afforded the pure product as a yellowish liquid (67% yield). $^1$H NMR (250 MHz, CDCl$_3$): δ 6.49 (dd, J=14.4 Hz, J'=6.2 Hz, 1H), 6.18 (dd, J=14.3 Hz, J'=1.2 Hz, 1H), 3.97 (m, 1H), 1.48 (m, 2H), 0.91 (t, J=8.1 Hz, 9H), 0.84 (t, J=7.5 Hz, 3H), 0.59 (q, J=8.8 Hz, 6H). $^{13}$C NMR (125 MHz, CDCl$_3$): δ 148.996, 76.258, 75.813, 30.395, 9.271, 6.780, 4.814.

Example 2

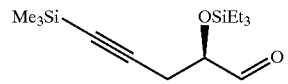

Step 1. To a solution of trimethylsilyl acetylene (2.50 ml, 17.74 mmol) in THF (20 ml) at −78° C. was added dropwise a 2.0 M solution of n-butyl lithium in pentane (8.8 ml, 17.6 mmol) and the reaction was stirred for 10 minutes. BF$_3$Et$_2$O complex (2.25 ml, 17.6 mmol) was then added and the stirring was continued for 10 minutes at −78° C. Finally a solution of the protected glycidol (Example 1) (3.34 g, 17.74 mmol) in THF (10 ml) was added by a canula and the reaction was stirred at −78° C. for 30 minutes. The resulting mixture was then quenched with a solution of saturated ammonium chloride and the product was extracted with ether, washed with brine, dried and concentrated. Flash column chromatography (silica gel, 20% ethyl acetate/hexanes) afforded the pure product as a colorless liquid in 63% yield. $^1$H NMR (250 MHz, CDCl$_3$): δ 3.76 (m, 1H), 3.70 (dd, J=9.9 Hz, J'=4.3 Hz, 1H), 3.59 (dd, J=10.0 Hz, J'=5.8 Hz, 1H), 2.43 (dd, J=5.7, J'=2.3 Hz, 1H), 0.92 (t, 7.8 Hz, 9H), 0.58 (q, J=7.8 Hz, 6H), 0.30 (s, 9H). $^{13}$C NMR (62 MHz, CDCl$_3$): δ 102.796, 70.155, 65.071, 63.602, 24.489, 6.704, 5.793, 4.345, 0.003.

Step 2: To a solution of the alcohol product of Step 1 (3.49 g, 12.2 mmol) in CH$_2$Cl$_2$ (36 ml) were added dropwise at 0° C. 2,6-Lutidine (3.2 ml, 26.8 mmol) and tertbutyldimethylsilyloxy triflate (4.1 ml, 18.3 mmol). The reaction mixture was warmed up to room temperature and stirred for 4 hours.

The solution was then poured into a solution of saturated NH₄Cl and extracted with diethyl ether. The combined extracts were dried and concentrated. Flash column chromatography (silica gel, 5% ethyl acetate/hexanes) afforded the pure product in quantitative yield. $^1$H NMR (250 MHz, CDCl₃): δ 3.88 (q, J=5.7, 1H), 3.52 (d, J=5.8 Hz, 2H), 2.51 (dd, J=16.9 Hz, J'=6.0 Hz, 1H), 2.38 (dd, J=16.5 Hz, J'=5.8 Hz, 1H), 1.12 (t, J=8.4 Hz, 9H), 0.98 (s, 9H), 0.69 (q, J=8.1 Hz, 6H), 0.30 (s, 9H), 0.18 (s, 3H), 0.12 (s, 3H). $^{13}$C NMR (62 MHz, CDCl₃): δ 104.760, 85.843, 72.270, 72.108, 66.744, 66.367, 25.926, 6.801, 4.425, 0.108, −4.389, −4.573.

Step 3: To a 0.1 M solution of protected diol from Step 2 (3.1 g, 7.75 mmol) in a 1:1 mixture of CH₂Cl₂:MeOH (78 ml) cooled at −10° C. was added camphor sulfonic acid (1.80 g, 7.75 mmol) and the reaction was stirred at that temperature for 0.5 h. The reaction mixture was then treated with triethyl amine (4.7 ml, 33 mmol), concentrated and purified by column chromatography (silica gel, 30% ethyl acetate/hexanes) affording pure product as a colorless liquid in 80% yield. $^1$H NMR (360 MHz, CDCl₃): δ 3.91 (q, J=5.4, 1H), 3.62 (dd, J=15.9 Hz, J'=5.6 Hz, 1H), 3.51 (dd, J=15.7 Hz, J'=5.4 Hz, 1H), 2.45 (m, 2H), 0.89 (s, 9H), 0.30 (s, 9H), 0.18 (s, 3H), 0.12 (s, 3H). $^{13}$C NMR (62 MHz, CDCl₃): δ 103.242, 86.710, 71.471, 66.070, 25.768, 25.191, 18.041, −0.127, −4.832

Step 4: To a 2.0 M solution of oxalyl chloride in dichloromethane (4.6 ml, 9.2 mmol) was added dropwise at −78° C. to a solution of DMSO (0.96 ml, 12.4 mmol) in 15 ml of dichloromethane. The reaction was stirred for 15 minutes at −78° C. and then a solution of the alcohol from Step 3(1.77 g, 6.19 mmol) in dichloromethane (20 ml) was added through a canula. Stirring was continued for 45 minutes at −78° C. The solution was then treated with triethylamine (4.1 ml, 29.6 mmol). The reaction mixture was allowed to warm to room temperature and then was quenched with water and the product was extracted with ether, washed with brine, dried and concentrated. Flash column chromatography (silica gel, 5% ethyl acetate/hexanes) afforded the product as a colorless liquid in 87% yield. $^1$H NMR (360 MHz, CDCl₃): δ 9.60 (s, 1H), 4.09 (m, 1H), 2.60 (dd, J=15.2 Hz and 5.6 Hz, 1H), 2.43 (dd, J=15.3 Hz and 10.1 Hz, 1H), 0.97 (s, 9H), 0.27 (s, 9H), 0.18 (s, 3H), 0.12 (s, 3H). $^{13}$C NMR (90 MHz, CDCl₃): δ 204.187, 103.427, 86.509, 70.633, 25.741, 25.276, 18.647, −0.109, −4.257.

Example 3

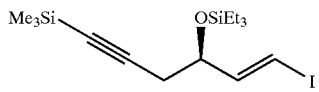

To a suspension of anhydrous CrCl₂ (2.058 g, 16.74 mmol) in THF (8 ml) was added at 0° C. a solution of iodoform (2.225 g, 5.65 mmol) in THF (6 ml) and a solution of the aldehyde of Example 2 (586 mg, 2.10 mmol) in THF (4 ml) by a double-tipped needle. The resulting mixture was stirred for 2 hours at 0° C. and for 2 hours at room temperature. It was then poured into water, extracted with ethyl acetate and washed with brine. The combined extracts were dried and concentrated. Flash column chromatography (silica gel, hexanes) afforded the pure product as a yellowish liquid (67% yield). $^1$H NMR (250 MHz, CDCl₃): δ 6.60 (dd, J=14.4 Hz and 5.8 Hz, 1H), 6.30 (dd, J=14.1 Hz and 1.4 Hz, 1H), 4.18 (q, J=6.3 Hz, 1H), 2.36 (m, 2H), 0.88 (s, 9H), 0.18 (s, 9H), 0.06 (s, 3H), 0.04 (s, 3H). $^{13}$C NMR (62 MHz, CDCl₃): δ 147.399, 102.986, 87.248, 77.126, 73.768, 29.356, 25.892, −0.111, −4.589.

Example 4

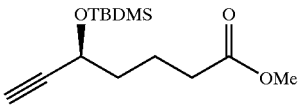

Step 1. To a stirred suspension of aluminum trichloride (5.57 g, 41.8 mmol) in methylene dichloride (35 ml) at −5° C. was added by cannula a solution of methyl-4-chloroformyl butanoate (3.6 ml, 26.12 mmol) in methylene dichloride (7 ml). After stirring for 30 minutes the suspension was transferred by a thick cannula to a solution of bis(trimethylsilyl) acetylene (5.9 ml, 26.12 mmol) in methylene dichloride (15 ml) cooled at −10° C. After stirring for 4 hours the resulting suspension was treated with ice-cold diluted hydrochloric acid (0.1 M) to dissolve the aluminium salts. The organic phase was separated and the aqueous layer was extracted with ether. Combined extracts were washed with brine, dried and concentrated. Flash column chromatography (silica gel, 10% ethyl acetate in hexanes) affords pure product in 64% yield. $^1$H NMR (360 MHz, CDCl₃): δ 3.64 (s, 3H), 2.61 (t, J=7.0 Hz, 2H), 2.33 (t, J=7.0 Hz, 2H), 1.93 (q, J=7.0 Hz, 2H), 0.20 (s, 9H). $^{13}$C NMR (62 MHz, CDCl₃): δ 186.430, 173.190, 101.530, 97.621, 51.316, 43.935, 32.327, 18.563, −1.293.

Step 2. To a 0.5 M solution of (S)-Alpine Borane in THF (44 ml, 22 mmol) at 0° C. was slowly added by cannula a solution of the keto-ester from Step 1 (3.42 g, 15.1 mmol) in THF (5 ml). The mixture was then stirred at room temperature for 18 hours. After cooling to 0° C., acetaldehyde (3.75 ml) was injected to destroy the excess reagent. After 5 minutes of stirring at 0° C., diethyl ether (10 ml) was added followed by the dropwise addition of ethanolamine (1.35 ml). The resulting solution was diluted with ether and washed with saturated sodium chloride. The ether portion was dried and concentrated. Flash column chromatography (silica gel, 30% ethyl ether in hexanes) affords the pure product in 84% yield and 90% ee (determined by preparation of its Mosher ester and analyzing the $^{19}$F NMR spectra). $^1$H NMR (250 MHz, CDCl₃): δ 4.32 (m, 1H), 3.63 (s, 3H), 2.33 (t, J=7.0 Hz, 2H), 1.71 (m, 4H), 0.12 (s, 9H). $^{13}$C NMR (62 MHz, CDCl₃): δ 174.056, 106.365, 89.453, 62.207, 51.417, 37.030, 33.742, 20.526, −0.419.

Step 3. To a solution of hydroxy-ester from Step 2 (2.1 g, 9.2 mmol) in CH₂Cl₂ (36 ml) was added dropwise at 0° C. 2,6-lutidine (2.4 ml, 20.2 mmol) and tert-butyldimethylsilyloxy triflate (3.2 ml, 13.8 mmol). The reaction mixture was warmed up to room temperature and stirred for 4 hours. The resulting solution was then poured into a solution of saturated NH₄Cl and extracted with diethyl ether. The combined extracts were dried and concentrated. Flash column chromatography (silica gel, 5% ethyl acetate/hexanes) afforded the pure product as a colorless liquid in 95% yield. $^1$H NMR (250 MHz, CDCl₃): δ 4.31 (t, J=6.2 Hz, 1H), 3.64 (s, 3H), 2.32 (t, J=7.0 Hz, 2H), 1.68 (m, 4H), 0.86 (s, 9H), 0.12 (s, 9H), 0.10 (s, 3H), 0.07 (s, 3H). $^{13}$C NMR (62 MHz, CDCl₃): δ 174.046, 107.384, 88.704, 62.931, 51.453, 37.667, 33.497, 25.778, 20.780, −0.407, −4.506, −5.065.

Step 4. Protected hydroxy-ester from Step 3 (3.0 g, 8.3 mmol) in THF/EtOH (16 ml/8 ml) was treated with a solution of silver nitrate (5.63 g, 33 mmol) in water/EtOH (8 ml/8 ml) at 0° C. The resulting yellow solid suspension was allowed to warm to 25° C. and it was then treated with a solution of potassium cyanide (3.78 g, 58 mmol) in water (8 ml). The product was extracted with ether, washed with brine, dried and concentrated. Flash column chromatography (silica gel, 10% ethyl acetate/hexanes) afforded the pure product as a colorless liquid in 89% yield. $^1$H NMR (360 MHz, CDCl$_3$): 4.33 (t, J=6.2 Hz, 1H), 3.64 (s, 3H), 2.35 (s, 1H), 2.32 (t, J=7.0 Hz, 2H), 1.70 (m, 4H), 0.89 (s, 9H), 0.12 (s, 3H), 0.10 (s, 3H). $^{13}$C NMR (62 MHz, CDCl$_3$): δ 173.943, 85.166, 72.432, 62.262, 51.549, 37.735, 33.598, 25.624, 20.694, 18.202, −4.670, −5.250.

Example 5

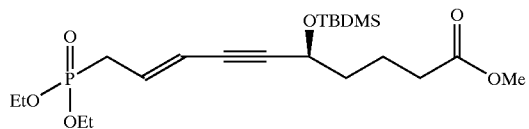

Step 1: To 0.5 g (2.5 mmol) of 3-bromo-propene bromide in 0.83 g (5 mmol) was added triethylphosphite (neat) and the mixture was heated to 120° C. for 3 hr. The excess phosphate was removed under vacuul and used directly in next step.

Step 2: To a solution of the phosphonate product of Step 1 (257 mg, 1.0 mmol) in 7 ml dry benzene, was added 270 mg (1.0 mmol) the alkyne from Example 4, (230 mg, 0.2 mmol), tetrakis(triphenyl phosphine) palladium, 76 mg (0.4 mmol), copper(I) iodide, and triethylamine (1.01 g, 10 mmol). The mixture was stirred at room temperature, over night. Removal of the solvent and column chromatography (1% MeOH in diethyl ether) gave the product (220 mg, 60%). This compound exhibited satisfactory spectroscopic and analytical data.

Example 6

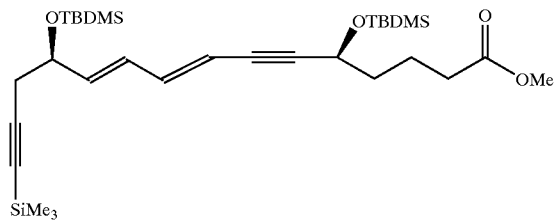

To a solution of phosphonate from Example 5 (217 mg 0.486 mmol) in 3 ml dry THF, cooled to −78° C. was added 0.51 ml 1M sodium bis(trimethylsily)amide (0.51 mmol). The reaction mixture was stirred for 3 min and the TBDMS protected aldehyde, prepared according to Example 3 (136 mg, 0.5 mmol) in 2.5 ml THF was added The mixture was stirred at −78° C. for 3 hrs, warmed up to room temperature, and stirred for another 30 mins. Sat. NH4Cl aqueous solution was added, and the mixture was extracted with ether. Removal of the solvent under vacuum and column chromatography (3% ethyl acetate in hexanes) gave 120 mg (43%) of the product.

Example 7

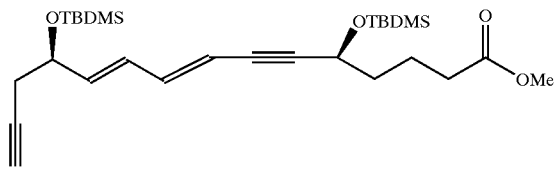

To a solution of the product of Example 7 (127 mg, 0.22 mmol) in THF/EtOH (2 ml/1 ml) was added a solution of silver nitrate (106 mg, 0.63 mmol) in water/EtOH (1 ml/1 ml) at 0° C. The resulting yellow solid suspension was allowed to warm to 25° C. and it was then treated with a solution of potassium cyanide (71 mg, 1.09 mmol) in water (1 ml). The product was extracted with ether, washed with brine, dried and concentrated. Flash column chromatography (silica gel, 4% diethyl ether/hexanes) afforded the pure product as a colorless liquid in 89% yield. $^1$H NMR (250 MHz, C$_6$D$_6$): δ 6.58 (dd, J=15.3 Hz and 10.9 Hz, 1H), 6.14 (dd, J=16.0 and 11.0 Hz, 1H), 5.65 (dd, J=16.3 Hz and 6.3 Hz, 1H), 5.56 (d, J=16.0 Hz, 1H), 4.52 (t, J=7.5 Hz, 1H), 4.20 (q, J=6.4 Hz, 1H), 3.34 (s, 3H), 2.20 (m, 4H), 2.12 (t, J=1.4 Hz, 1H), 1.78 (m, 4H), 1.03 (s, 9H), 0.97 (s, 9H), 0.25 (s, 3H), 0.17 (s, 3H), 0.06 (s, 3H), 0.02 (s, 3H). $^{13}$C NMR (62 MHz, CDCl$_3$): δ 173.891, 140.738, 137.433, 129.200, 111.125, 93.363, 83.432, 80.947, 71.306, 70.197, 63.012, 51.452, 37.889, 33.516, 28.296, 25.792, 20.566, 18.075, −4.419, −4.578, −4.861, −5.014.

Example 8

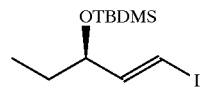

Prepared similarly to Example 1. The product gave satisfactory spectroscopic data.

Example 9

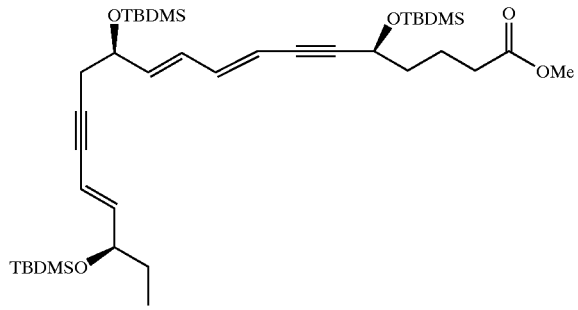

It was prepared from the vinyl iodide of Example 1 and the alkyne of Example 7 using the coupling procedure of Example 5 (Step 2). $^1$H NMR (500 MHz, C$_6$D$_6$): δ 6.59 (dd, J=15.2 Hz and 10.9 Hz, 1H), 6.24 (dd, J=15.2 and 11.0 Hz, 1H), 6.14 (dd, J=15.5 Hz and 5.3 Hz, 1H), 5.86 (d, J=15.4 Hz, 1H), 5.67 (dd, J=14.8 Hz and 5.6 Hz, 1H), 5.59 (d, J=15.5 Hz, 1H), 4.54 (t, J=5.7 Hz, 1H), 4.24 (q, J=5.9 Hz, 1H), 3.94 (q, J=5.6 Hz, 1H), 3.35 (s, 3H), 2.46 (m, 2H), 2.17 (t, J=7.1 Hz, 2H), 1.84 (m, 4H), 1.44 (m, 2H), 1.04 (s, 9H), 1.02 (s, 9H), 1.00 (s, 9H), 0.86 (t, J=7.5 Hz, 3H), 0.28 (s, 3H), 0.19 (s, 3H), 0.14 (s, 3H), 0.08 (s, 3H), 0.07 (s, 3H), 0.05 (s, 3H). $^{13}$C NMR (125 MHz, C$_6$D$_6$): δ 173.131, 145.665, 141.248, 138.411, 129.420, 111.518, 109.904, 93.989, 87.526, 84.119, 81.048, 73.998, 72.025, 63.570, 50.913, 38.321, 33.587, 31.253, 29.235, 26.014, 21.163, 18.413, 9.221, −4.207, −4.421, −4.603, −4.621, −4.772, −5.094.

Example 10

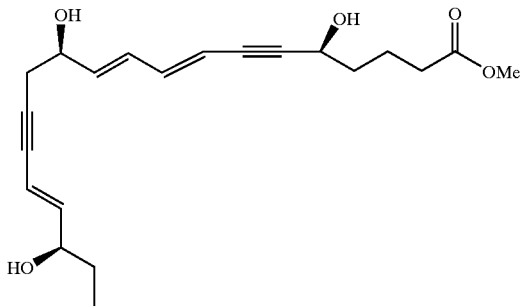

A solution of the product of Example 9 (40 mg, 0.065 mmol) in THF (1 ml) was treated with 1.0 M TBAF (0.32 ml, 0.32 mmol) at 0° C. The reaction was stirred for 3 h and then poured into water and extracted with ether. The ether extracts were washed with brine, dried and concentrated. The ethereal solution was then treated with an excess of freshly prepared diazomethane in ether to convert the free acid to the product. Flash column chromatography (silica gel, 4% MeOH/CH$_2$Cl$_2$) afforded the pure product in 90% yield. $^1$H NMR (500 MHz, C$_6$D$_6$): δ 6.55 (dd, J=15.5 Hz and 10.9 Hz, 1H), 6.16 (dd, J=15.2 Hz and 11.0 Hz, 1H), 6.05 (dd, J=15.5 Hz and 5.3 Hz, 1H), 5.70 (d, J=16.2 Hz, 1H), 5.61 (dd, J=14.6 Hz and 5.5 Hz, 1H), 5.58 (d, J=14.7 Hz, 1H), 4.28 (t, J=5.8 Hz, 1H), 4.06 (dd, J=11.2 Hz and 5.3 Hz, 1H), 3.65 (dd, J=11.0 Hz and 6.7 Hz, 1H), 3.30 (s, 3H), 2.36 (m, 2H), 2.06 (t, J=6.9 Hz, 2H), 1.72 (m, 2H), 1.59 (m, 2H), 1.27 (m, 2H), 0.74 (t, J=7.4 Hz, 3H). $^{13}$C NMR (125 MHz, C$_6$D$_6$): δ 173.819, 145.219, 141.143, 136.647, 130.007, 111.340, 109.915, 92.672, 85.857, 84.082, 81.330, 73.505, 70.225, 62.533, 51.488, 37.097, 33.599, 29.912, 28.658, 20.615, 9.451. HPLC: Beckman Ultrasphere reverse phase column (30% water in MeOH, 3.8 ml/min, 252 bar): elution time=5.41 min.

Example 11

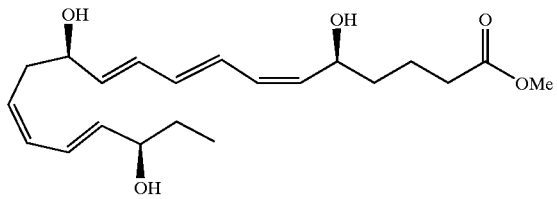

To a solution of the bis-acetylenic product from Example 10 (7.7 mg, 0.021 mmol) in dichloromethane (4 ml) was added Lindlar catalyst (1.5 mg, 20% by weight), quinoline (4 μl), and the reaction mixture was stirred under the static atmosphere of hydrogen. Samples were taken every 20 minutes for HPLC analysis (30% water in MeOH), and the reaction was stopped at 60% conversion. The resulting solution was filtrated over a pad of celite and separated by HPLC (45% water in MeOH) affording the pure product in 60% yield. $^1$H NMR (500 MHz, C$_6$D$_6$) δ 6.54 (dd, J=14.8 Hz and 11.5 Hz, 1H), 6.49 (dd, J=14.9 Hz and 11.7 Hz, 1H), 6.26 (dd, J=16.0 Hz and 10.5 Hz, 1H), 6.11 (t, J=9.2 Hz, 1H), 6.09 (dd, J=14.7 Hz and 11.1 Hz, 1H), 5.95 (t, J=11.0 Hz, 1H), 5.60 (dd, J=15.4 Hz and 6.4 Hz, 1H), 5.56 (dd, J=14.9 Hz and 6.0 Hz, 1H), 5.42 (dt, J=10.8 Hz and 8.1 Hz, 1H), 5.30 (t, J=10.6 Hz, 1H), 4.38 (q, J=7.8 Hz, 1H), 4.03 (q, J=6.6 Hz, 1H), 3.83 (q, J=6.6 Hz, 1H), 3.30 (s, 3H), 2.2–2.4 (m, 4H), 2.08 (t, J=6.9 Hz, 2H), 1.6–1.7 (m, 2H), 1.3–1.5 (m, 2H), 0.85 (t, J=6.7 Hz, 3H). $^{13}$C NMR (125 MHz, C$_6$D$_6$): δ 177.135, 137.855, 137.106, 134.923, 134.057, 131.093, 130.273, 129.637, 128.428, 126.868, 125.269, 73.554, 71.747, 67.609, 37.123, 36.223, 33.835, 30.576, 21.165, 9.867. HPLC: Beckman Ultrasphere reverse phase column (30% water in MeOH, 3.8 ml/min, 254 bar): elution time= 8.43 min.

Example 13

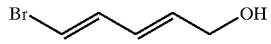

Step 1: To a 7.4 M solution of KOH (31.0 g, 553 mmol) in water (75 ml) cooled to −20° C. was added pyridinium-1-sulfonate (21.6 g, 136 mmol) and the reaction was strirred for 1 h at −20° C. and then for 4 h at room temperature. The reaction mixture was then heated for ½ h at 40° C. before being cooled to 0° C. The brownish precipitate was filtrated off, washed with acetone and then recrystalized from methanol affording pure product as a yellow-orange crystals (11.3 g, 82.96 mmol, 61% yield). $^1$H NMR (360 MHz, DMSO): δ 9.05 (d, J=9.5 Hz, 2H), 7.00 (t, J=13.8 Hz, 1H), 5.05 (dd, J=13.5 Hz and 9.1 Hz, 2H).

Step 2: To a solution of PPh$_3$ (21.57 g, 82.4 mmol) in CH$_2$Cl$_2$ (500 ml) cooled at 0° C. was directly added NBS (14.67 g, 82.4 mmol). After the addition was completed the reaction was stirred at room temperature for 45 minutes. At this point potassium glutaconaldehyde salt from step 1 (5.6 g, 41.2 mmol) was directly added and the resulting solution was stirred at room temperature for 7 h. The reaction mixture was then poured into a buffer solution at pH 7.0 and extracted with CH$_2$Cl$_2$. The combined extracts were then dried and concentrated. Flash column chromatography (silica gel, 2% triethylamine/10% diethyl ether/hexanes) afforded the product as colorless liquid (3.27 g, 20.35 mmol, 49% yield). $^1$H NMR (250 MHz, CDCl$_3$): δ 9.18 (d, J=7.8 Hz, 1H), 6.17 (dd, J=13.2 Hz and 11.0 Hz, 1H), 5.95 (d, J=13.8 Hz, 1H), 5.86 (dd, J=15.4 Hz and 10.9 Hz, 1H), 5.62 (dd, J=15.3 Hz and 7.5 Hz, 1H). $^{13}$C NMR (62 MHz, CDCl$_3$): δ 191.965, 146.490, 135.457, 132.172, 118.633.

Step 3. To a solution of the dienal (4.14) (0.9 g, 5.59 mmol) in methanol (15 ml) was added CeCl$_3$ (1.38 g, 5.59 mmol) and NaBH$_4$ (0.2.1 g, 5.59 mmol). After five minutes the reaction was treated with a diluted solution of HCl until neutral pH and extracted with ether. The combined extracts were then dried and concentrated. Flash column chromatography (silica gel, 20% ethyl acetate/hexanes) afforded the product as a colorless liquid (0.80 g, 4.98 mmol, 89% yield). $^1$H NMR (250 MHz, CDCl$_3$): δ 6.71 (dd, J=13.5 Hz and 10.6 Hz, 1H), 6.30 (d, J=13.8 Hz, 1H), 6.17 (dd, J=14.5 Hz and 9.7 Hz, 1H), 5.84 (dt, J=14.6 Hz and 6.1 Hz, 1H), 4.14 (d, J=4.6 Hz, 2H). $^{13}$C NMR (62 MHz, CDCl$_3$): δ 136.698, 133.278, 128.087, 108.994, 62.750.

Example 14

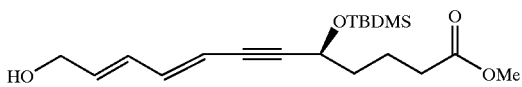

To a solution of vinyl bromide from Example 13 (0.74 g, 4.51 mmol) in Et$_2$NH (8 ml) was added Pd(PPh$_3$)$_4$ (160 mg, 0.14 mmol) and the solution protected from light was stirred for 45 minutes at room temperature. A small amount of benzene (4 ml) was added to completely dissolve the catalyst. To the resulting homogeneous solution was then added through a canula a solution of the alkyne from Example 4 (1.25 g, 4.61 mmol) in Et$_2$NH (8 ml) and CuI (88 mg, 0.46 mmol). The mixture was stirred for 3 h at room temperature and quenched with a saturated aqueous solution of ammonium chloride and extracted with ether. It was then washed with brine, dried and concentrated. Flash column chromatography (silica gel, 20% ethyl acetate/hexanes) afforded the pure product as a colorless liquid (1.52 g, 4.33 mmol, 96% yield). $^1$H NMR (360 MHz, CDCl$_3$): δ 6.61 (dd, J=15.7 Hz and 10.6 Hz, 1H), 6.02 (dd, J=14.8 Hz and 10.9 Hz, 1H), 5.57 (d, J=14.4 Hz), 5.48 (dt, J=15.1 Hz and 5.2 Hz, 1H), 4.54 (m, 1H), 3.75 (s, 2H), 3.30 (s, 3H), 2.14 (t, J=7.0 Hz, 2H), 1.85 (m, 2H), 1.77 (m, 2H), 1.05 (s, 9H), 0.27 (s, 3H), 0.18 (s, 3H). $^{13}$C NMR (62 MHz, CDCl$_3$): δ 141.705, 136.071, 129.466, 111.138, 93.991, 84.393, 63.859, 62.789, 51.161, 38.516, 33.831, 26.244, 21.391, −3.936, −4.648.

Example 15

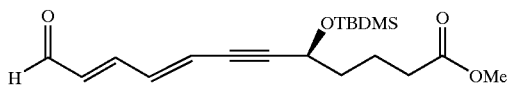

To a solution of dimethyl sulfoxide (0.66 ml, 8.5 mmol) in CH$_2$Cl$_2$ (40 ml) was added dropwise at −78° C. oxalyl chloride (0.56 ml, 6.4 mmol) and the reaction was stirred at that temperature for 15 minutes. Alcohol from Example 14 (1.5 g, 4.26 mmol) was added via a double-tipped needle and the resulting solution was stirred an additional 45 minutes at −78° C. Triethylamine (2.96 ml, 21.3 mmol) was added slowly to the cloudy white mixture that was allowed to warm up to room temperature and it was then poured into water and extracted with ethyl acetate. The combined extracts were dried and concentrated. Flash column chromatography (silica gel, 5% ethyl acetate/hexanes) afforded the pure product as a colorless liquid (1.31 g, 3.75 mmol, 87% yield). $^1$H NMR (360 MHz, C$_6$D$_6$): δ 9.50 (d, J=8.2 Hz, 1H), 6.31 (dd, J=14.7 Hz and 11.3 Hz, 1H), 6.22 (dd, J=14.6 Hz and 11.2 Hz, 1H), 5.77 (dd, J=14.9 Hz and 8.2 Hz, 1H), 5.59 (d, J=15.9 Hz, 1H), 4.50 (m, 1H), 3.34 (s, 3H), 2.16 (t, J=7.0 Hz, 2H), 1.85 (m, 2H), 1.76 (m, 2H), 1.04 (s, 9H), 0.26 (s, 3H), 0.18 (s, 3H). $^{13}$C NMR (62 MHz, CDCl$_3$): δ 191.944, 172.975, 148.566, 138.933, 133.120, 119.950, 98.691, 83.368, 63.524, 50.987, 38.019, 33.504, 25.921, 21.021, 18.370, −4.320, −4.931.

Example 16

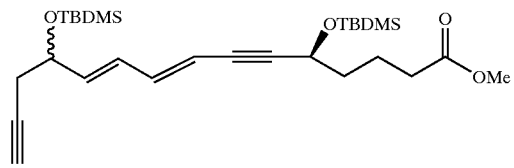

To a solution of the allenyl boronic acid (518 mg, 6.18 mmol) in toluene (20 ml) were added molecular sieves (3.0 g) and diisopropyl-D-tartrate (2.6 ml, 12.36 mmol) and the resulting solution was allowed to stand at room temperature for 24 h with gentle stirring from time to time. The obtained solution of chiral allenyl boronic ester was then canulated to a new flask and cooled at −78° C. At this point a solution of the aldehyde from Example 15 (665 mg, 1.9 mmol) in toluene (10 ml) was added through a double tipped needle and the reaction mixture was stirred at −78° C. for 12 h and then warmed up slowly at room temperature overnight. The resulting solution was then quenched with a diluted solution of HCl, extracted with ether and it was then washed with brine, dried and concentrated. Flash column chromatography (silica gel, 5% ethyl acetate/hexanes) afforded the pure product as a colorless liquid (592 mg, 1.52 mmol, 80% yield). To a solution of the obtained alcohol product (592 mg, 1.52 mmol) in CH$_2$Cl$_2$ (10 ml) were added dropwise at 0° C. 2,6-lutidine (0.40 ml, 3.34 mmol) and tert-butyldimethylsilyloxy triflate (0.41 ml, 2.28 mmol). The reaction mixture was warmed up to room temperature and stirred for 4 hours. The resulting solution was then poured into a solution of saturated NH$_4$Cl and extracted with diethyl ether. The combined extracts were dried and concentrated. Flash column chromatography (silica gel, 2% ethyl acetate/hexanes) afforded the pure product (4.4) as a colorless liquid in 95% yield. $^1$H NMR (250 MHz, CDCl$_3$): δ 6.52 (dd, J=15.5 Hz and 10.9 Hz, 1H), 6.26 (dd, J=15.2 and 11.0 Hz, 1H), 5.85 (dd, J=15.5 Hz and 5.3 Hz, 1H), 5.10 (d, J=16.2 Hz, 1H), 4.51 (t, J=5.6 Hz, 1H), 4.31 (q, J=5.9 Hz, 1H), 3.54 (s, 3H), 2.45 (m, 4H), 1.95 (t, J=1.4 Hz, 1H), 1.82 (m, 4H), 0.97 (s, 18H), 0.18 (s, 3H), 0.12 (s, 3H), 0.07 (s, 3H), 0.05 (s, 3H). $^{13}$C NMR (62 MHz, CDCl$_3$): δ 173.891, 140.738, 137.433, 129.200, 111.125, 93.363, 83.432, 80.947, 71.306, 70.197, 63.012, 51.452, 37.889, 33.516, 28.296, 25.792, 20.566, 18.075, −4.419, −4.578, −4.861, −5.014.

A number of embodiments of the invention have been described. Nevertheless, it will be understood that various modifications may be made without departing from the spirit and scope of the invention. Accordingly, other embodiments are within the scope of the following claims.

What is claimed is:

1. A method of preparing an eicosanoid compound of formula 21,

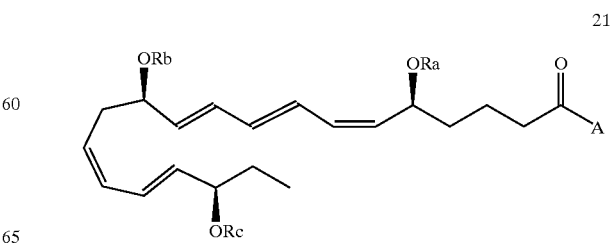

the method comprising:
 providing a compound of formula 22

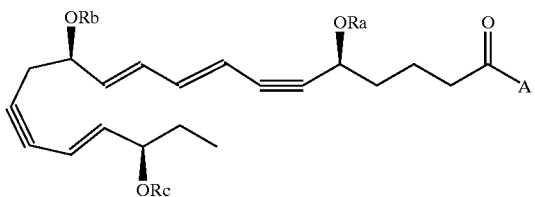

wherein:
 A is hydroxy, alkoxy, aryloxy, amino, alkylamino, dialkylamino, or —OM, where M is a cation selected from the group consisting of ammonium, tetra-alkyl ammonium, Na, K, Mg, or Zn; and
 Ra, Rb and Rc, are independently selected from the group consisting of hydrogen, alkyl, aryl, heteroaryl, acyl, silyl, alkoxyacyl and aminoacyl; and
performing selective hydrogenation on compound 22 to give compound 21.

2. A method of claim 1 where the selective hydrogenation is performed by hydrogen and Lindlar catalyst.

3. A method of claim 1, where Ra, Rb and Rc are H and A is OR, where R is selected from a group consisting of hydrogen, alkyl and aryl.

4. A method of preparing a compound of formula 22,

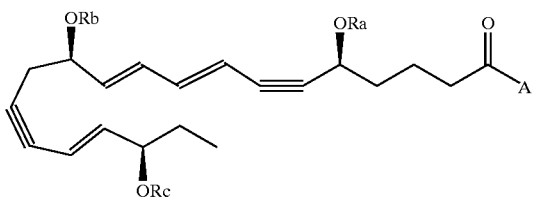

the method comprising:
 (a) providing a compound of formula 25 and a compound of formula 4

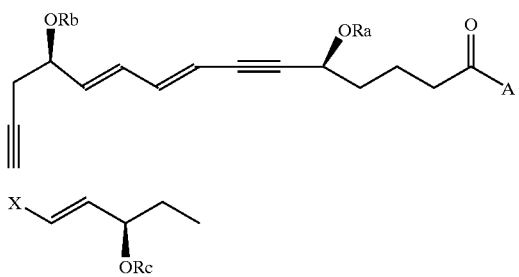

wherein:
 A is hydroxy, alkoxy, aryloxy, amino, alkylamino, dialkylamino, or —OM, where M is a cation selected from the group consisting of ammonium, tetra-alkyl ammonium, Na, K, Mg, or Zn;
 Ra, Rb and Rc, are independently selected from the group consisting of hydrogen, alkyl, aryl, heteroaryl, acyl, silyl, alkoxyacyl and aminoacyl; and
 X is Br or I; and (b) performing Sonogashira coupling among compound 25 and compound 4 to form compound 22.

5. A method of preparing an eicosanoid analog of formula 23,

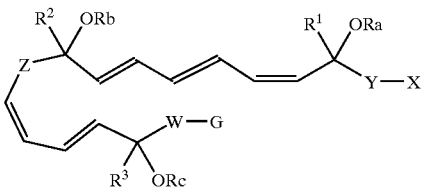

the method comprising:
 (a) providing a compound of formula 24

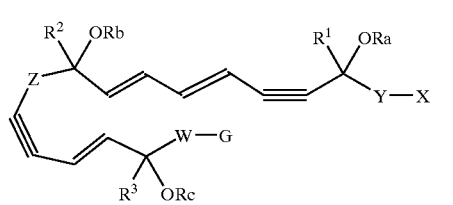

wherein:
 Ra, Rb and Rc, are independently selected from the group consisting of hydrogen, alkyl, aryl, heteroaryl, acyl, silyl, alkoxyacyl and aminoacyl;
 $R^1$, $R^2$ and $R^3$ are independently selected from the group consisting of hydrogen, alkyl, aryl and heteroaryl;
 X is selected from the group consisting of: —C(O)-A, —SO2-A, —PO(OR)-A, where A is hydroxy, alkoxy, aryloxy, amino, alkylamino, dialkylamino, or —OM, where M is a cation selected from a group consisting of ammonium, tetra-alkyl ammonium, Na, K, Mg, or Zn, and R is hydroxyl or alkoxy;
 Y, Z and W are linkers independently selected from the group consisting of a ring containing up to 20 atoms and a chain of up to 20 atoms, provided that Y, Z and W can independently include one or more nitrogen, oxygen, sulfur or phosphorous atoms, and further provided that Y, Z and W can independently include one or more substituents selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that Y, Z and W can also contain one or more fused carbocyclic, heterocyclic, aryl or heteroaryl rings, and provided that all linkers Y are connected to the adjacent C(R)OR group via a carbon atom; and
 G is selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido; and (b) performing selective hydrogenation on compound 24 to give compound 23.

6. A compound having the formula 22 or 24

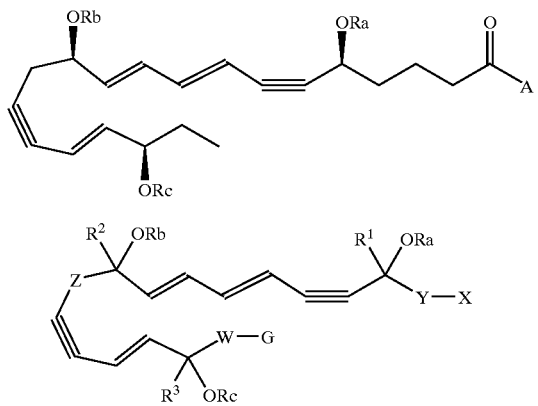

wherein:
A is hydroxy, alkoxy, aryloxy, amino, alkylamino, dialkylamino, or —OM, where
M is a cation selected from the group consisting of ammonium, tetra-alkyl ammonium, Na, K, Mg, and Zn;
Ra, Rb and Rc, are independently selected from the group consisting of hydrogen, alkyl, aryl, heteroaryl, acyl, silyl, alkoxyacyl and aminoacyl;
$R^1$, $R^2$ and $R^3$ are independently selected from the group consisting of hydrogen, alkyl, aryl and heteroaryl;
X is selected from the group consisting of:
—C(O)-A, —SO2-A, —PO(OR)-A, where A is hydroxy, alkoxy, aryloxy, amino, alkylamino, dialkylamino, or —OM, where M is a cation selected from the group consisting of ammonium, tetra-alkyl ammonium, Na, K, Mg, and Zn, and R is hydroxyl or alkoxy;
Y, Z and W are linkers independently selected from the group consisting of a ring containing up to 20 atoms and a chain of up to 20 atoms, provided that Y, Z and W can independently include one or more nitrogen, oxygen, sulfur or phosphorous atoms, and further provided that Y, Z and W can independently include one or more substituents selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that Y, Z and W can also contain one or more fused carbocyclic, heterocyclic, aryl or heteroaryl rings, and provided that all linkers Y are connected to the adjacent C(R)OR group via a carbon atom; and
G is selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido.

7. A pharmaceutical composition, comprising:
a compound according to claim 6; and
a pharmaceutically acceptable carrier.

8. A method of ameliorating or treating a disease or condition associated with inflammatory response, cardiovascular disease and abnormal cell proliferation or cancer, the method comprising:
administering to a subject an effective amount of a compound according to claim 6.

9. A method of ameliorating or treating a disease or condition associated with inflammatory response, cardiovascular disease and abnormal cell proliferation or cancer, the method comprising:
administering to a subject an effective amount of a pharmaceutical composition according to claim 7.

* * * * *

UNITED STATES PATENT AND TRADEMARK OFFICE
CERTIFICATE OF CORRECTION

PATENT NO. : 6,949,664 B2
APPLICATION NO. : 10/405924
DATED : September 27, 2005
INVENTOR(S) : Nicos A. Petasis It is certified that error appears in the above-identified patent and that said Letters Patent is hereby corrected as shown below:

On page 1, line 13, delete "The U.S. Government may have certain right this invention pursuant to Grant No. PO1-DE13499 (Subcontract) awarded by the National Institutes of Health."

and insert --This invention was made with government support under Contract No. P01 DE013499 awarded by the National Institutes of Health. The government has certain rights in the invention.--

Signed and Sealed this

Eighth Day of September, 2009

David J. Kappos
*Director of the United States Patent and Trademark Office*